United States Patent

Diehl et al.

[11] 4,017,299
[45] Apr. 12, 1977

[54] PHTHALIMIDE DERIVATIVES AS PLANT GROWTH REGULANTS

[75] Inventors: Robert Eugene Diehl, Trenton; Bryant Leonidas Walworth, Pennington, both of N.J.

[73] Assignee: American Cyanamid Company, Stamford, Conn.

[22] Filed: July 23, 1975

[21] Appl. No.: 598,458

Related U.S. Application Data

[60] Division of Ser. No. 382,418, July 25, 1973, Pat. No. 3,940,419, which is a continuation-in-part of Ser. No. 348,355, April 5, 1973, abandoned, which is a continuation-in-part of Ser. No. 282,537, Aug. 21, 1972, abandoned.

[52] U.S. Cl. .................................. 71/96; 47/57.6
[51] Int. Cl.² ........................................ A01N 9/22
[58] Field of Search .............. 71/95, 96; 47/57.6

[56] References Cited

UNITED STATES PATENTS

| 2,783,245 | 2/1957 | Weidenheimer et al. | 260/326 A |
|---|---|---|---|
| 2,999,863 | 9/1961 | Upham | 260/326 A |
| 3,457,063 | 7/1969 | Neighbors | 71/96 X |
| 3,634,452 | 1/1972 | Fischer et al. | 71/96 X |
| 3,712,907 | 1/1973 | Gilch et al. | 260/326 A |

*Primary Examiner*—Joseph Paul Brust
*Attorney, Agent, or Firm*—H. G. Jackson

[57] ABSTRACT

The invention is a novel class of phthalimido derivatives represented by a formula:

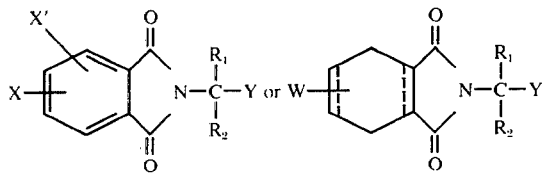

wherein W is hydrogen or alkyl $C_1$-$C_4$; X and X' each represent hydrogen, halogen, alkyl $C_1$-$C_4$, $CF_3$, alkoxy($C_1$-$C_4$), benzyloxy, di($C_1$-$C_4$)alkylamino, $C_1C_4$ alkylthio, hydroxy, $C_1$-$C_4$ alkylsulfonyl, alkanoylamino $C_1$-$C_4$ or nitro; Y is —$COOR_3$, —$CONHR_8$, —$CONR_3$ $R_4$, —$CONHN(R_5)_2$, —$CONHN^+(R_6)_3$ . halide⁻, —CN or —$CCR_7$ with the proviso that at least one of X and X' is a substituent other than hydrogen; $R_1$ and $R_2$ each represent alkyl $C_1$-$C_4$ or when taken together with the carbon to which they are attached form cycloalkyl $C_4$-$C_{11}$ optionally substituted with methyl; $R_3$ and $R_4$ each represent hydrogen or alkyl $C_1$-$C_4$; $R_5$ and $R_6$ each represent alkyl $C_1$-$C_2$; $R_7$ is halogen and $R_8$ is —$CH_3$ or

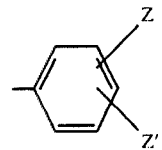

where Z and Z' are hydrogen, alkyl $C_1$-$C_2$, halogen, —$CF_3$ or —$OCH_3$, ==== is a single or double bond with the proviso that there be only 0 or 1 double bond in the ring and a method for regulating the growth of plants with these compounds and with compounds having the above structure wherein X and X' each represent hydrogen.

10 Claims, No Drawings

PHTHALIMIDE DERIVATIVES AS PLANT GROWTH REGULANTS

CROSS REFERENCE TO RELATED APPLICATIONS

This application is a division of Ser. No. 382,418 filed July 25, 1973 which is now U.S. Pat. No. 3,940,419 (Feb. 24, 1976). Serial No. 383,418 is a continuation in part of Ser. No. 348,355 filed Apr. 5, 1973 and now abandoned which is a continuation in part of Ser. No. 282,537 filed Aug. 21, 1972 which is also abandoned.

BACKGROUND OF THE INVENTION

1. Field of the Invention

The invention pertains to the chemical arts, i.e., phthalimide derivatives and their use as plant growth regulants.

2. Description of the Prior Art

Upham's U.S. Pat. No. 2,999,863 (1961) discloses alpha-phthalimidoacetamide derivatives as anticonvulsants and a method for their manufacture.

SUMMARY OF THE INVENTION

In invention is novel compounds represented by a formula:

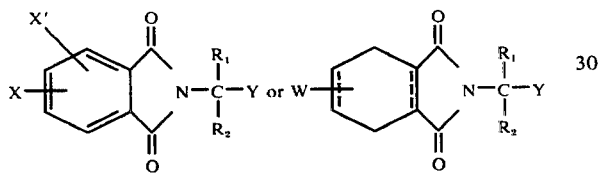

wherein W is hydrogen or alkyl $C_1$–$C_4$; X and X' each represent hydrogen, halogen, alkyl $C_1$–$C_4$, $CF_3$, alkoxy($C_1$–$C_4$), benzyloxy, di($C_1$–$C_4$) alkylamino, $C_1$–$C_4$ alkylthio, hydroxy, $C_1$–$C_4$ alkylsulfonyl, alkanoylamino $C_1$–$C_4$ or nitro; Y is —COOR, —CONHR$_8$, —CONR$_3$R$_4$, —CONHN(R$_5$)$_2$, —CONHN$^+$(R$_6$)$_3$ · halide$^-$, —CN or —COR$_7$ with the proviso that at least one of X and X' is a substituent other than hydrogen; R$_1$ and R$_2$ each represent alkyl $C_1$–$C_4$ or when taken together with the carbon to which they are attached form cycloalkyl $C_4$–$C_{11}$ optionally substituted with methyl R$_3$ and R$_4$ each represent hydrogen or alkyl $C_1$–$C_4$; R$_5$ and R$_6$ each represent alkyl $C_1$–$C_2$; R$_7$ is halogen and R$_8$ is —CH$_3$

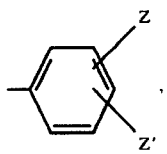

where Z and Z' are hydrogen, halogen, alkyl $C_1$—$C_2$, —$CF_3$ or —$OCH_3$, ⁼⁼⁼ is a single or double bond with the proviso that there be only 0 or 1 double bond in the ring; mixtures of said compounds are also within the scope of our invention. Isomeric mixtures of the above-identified compounds are also contemplated and are of particular interest in this invention. These compounds, as well as compounds of the above structure where X and X' are both hydrogen, are useful as plant growth regulating agents, as intermediates for the preparation of plant growth regulating agents, or as both plant growth regulants and intermediates therefore. Compounds of the above structure where Y is —COR$_7$ and X, R$_1$, R$_2$ and R$_7$ are as described, are primarily useful as intermediates for the preparation of the plant growth regulating agents. Similarly, compounds having the above formula where Y is —COOR$_3$ and R$_3$ is hydrogen, are also useful as intermediates; however, many of these compounds are also highly effective plant growth regulants.

DETAILED DESCRIPTION

In accordance with the invention, the above-identified phthalimido derivatives can be prepared by reacting the appropriate α-aminocarboxylic acid or acid derivative with a phthalic anhydride, preferably in the presence of an aprotic solvent and a tertiary amine, such as triethylamine. Among the solvents which are useful in carrying out this reaction are: toluene, xylene, dimethylformamide and acetic acid. In practice, it will be found that the reaction can be conducted at a temperature between about 100° C. and 175° C., and preferably between 100° C. and 150° C. Alternatively the required product can be prepared by fusing the α-amino acid or acid derivative and phthalic anhydride at temperatures between about 150° C. and 250° C., but preferably at 180° C. to 210° C. The reaction can be graphically illustrated as follows:

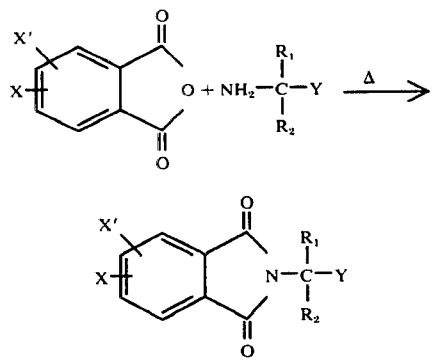

where X,X', R$_1$, R$_2$ and Y are as indicated above, with the exception that Y cannot be —COR$_7$ or —CONHN$^+$(R$_6$)$_3$ · halide $^-$. This reaction may also be employed for the preparation of the 1,2,3,6- or 3,4,5,6- tetrahydrophthalimide or 1,2,3,4,5,6- hexahydrophthalimido derivatives. Reaction conditions are the same as described above excepting that the appropriate tetrahydrophthalic or hexahydrophthalic anhydride is substituted for phthalic anhydride.

While this high temperature reaction described above is effective for the preparation of all of the above-identified compounds, we have discovered that when Y is —CN and the reaction is carried out at a temperature of about 60° C. or less, a phthalamic acid is formed which corresponds to the α,α-disubstituted-α-aminonitrile used. The phthalamic acid can then be cyclized to the corresponding phthalimidonitrile. This reaction is described in greater detail below. In the case where Y is —COCH, the thus-formed acid can then be converted to the corresponding acid halide by heating the acid with thionyl chloride, thionyl bromide, phosphorus pentachloride, or the like, preferably in the presence of an aprotic solvent, aromatic or chlorinated hydrocarbons, such as benzene, xylene, toluene, methylene chloride, chloroform of dichloroethane. The reaction is graphically illustrated below, wherein thionyl halide, i.e. chloride or bromide, is representative of the halogenating agent employed.

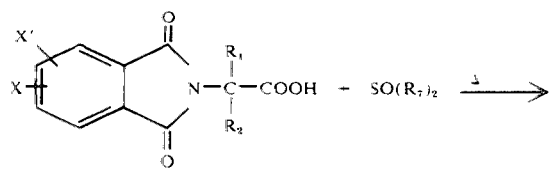

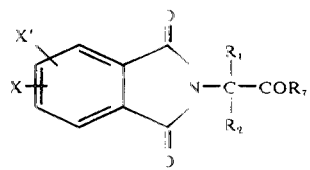

wherein X,X',R$_1$,R$_2$ and R$_7$ are as described above. Conversion of the (tetrahydrophthalimido) acetic acids and the (hexahydrophthalimido) acetic acids to their corresponding acid halides may also be achieved by the above reaction using the appropriate acid as starting material.

The thus-formed acid chloride or acid bromide can then be converted to the corresponding amide by reaction thereof with ammonia, dialkylamine or dialkyl hydrazine, at a temperature between about −20° C. and +25° C., and preferably −10° C. to +15° C. This reaction is preferably carried out by dissolving the acid halide in a solvent, such as acetone or a water-miscible ether, such as tetrahydrofuran, dioxane, or the like, and adding this solution to an aqueous solution of the amine. Alternatively, the amine can be added directly to a solution of the acid halide in the above solvents or in an aprotic solvent, such as toluene or chloroform. The reaction can be graphically shown as follows:

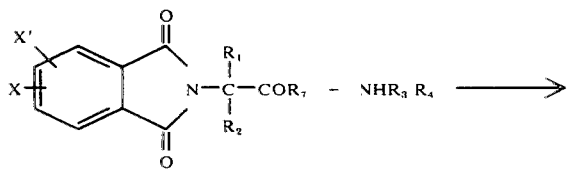

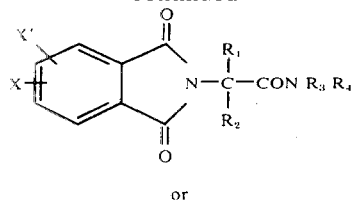

or

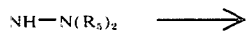

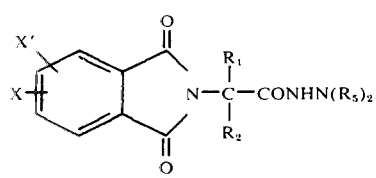

wherein X,X',R$_1$, R$_2$, R$_3$, R$_4$, R$_5$ and R$_7$ are as defined above.

Similarly, these reactions can be employed to prepare the (tetrahydrophthalimido) acetamides and the (hexahydrophthalimide) acetamides using the appropriate acid chloride as starting material.

Alternatively, the phthalimido acetamides in which R$_4$ is hydrogen may be prepared by reacting the appropriate phthalic, tetrahydro- or hexahydrophthalic anhydride with the appropriately α, α-disubstituted-α-aminonitrile to give the corresponding phthalamic acid. This reaction is carried out at temperatures from about 20° C. to 60° C. in an inert solvent such as ether, tetrahydrofuran, chloroform, methylene chloride, benzene, toluene, and the like. The thus-formed phthalamic acid is then cyclized to the corresponding phthalimide, tetra- or hexahydrophthalimidonitrile by heating with a dehydrating agent such as acetic anhydride, acetyl chloride, thionyl chloride or the like at temperatures from about 0° C. to 100° C. Hydration of the thus-formed phthalimidonatrile is preferably carried out with a strong acid such as sulfuric acid, preferably in the presence of a non-miscible solvent such as methylene chloride or chloroform and the like at temperatures from about −10° C. to +30° C. These reactions are graphically illustrated by using the substituted phthalic anhydride as an example as follows:

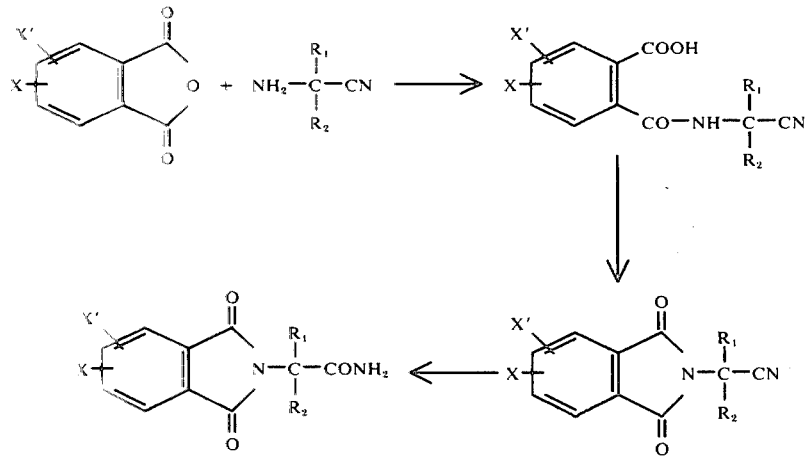

wherein X, X', R$_1$ and R$_2$ are as defined above.

Where a hydrazinium halide is desired, an amide having the formula:

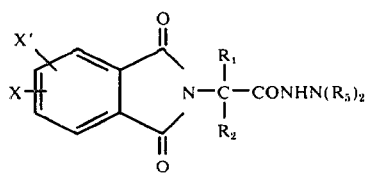

or

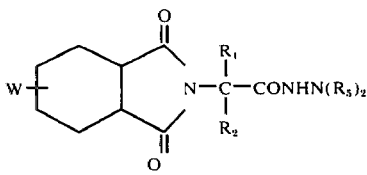

where W,X,X', $R_1$, $R_2$, $R_5$ and ═══ are as defined above, can be treated with an alkyl halide in the presence of a solvent, such as tetrahydrofuran, ether, dioxane, benzene, chloroform, or the like, at an elevated temperature to yield the desired corresponding hydrazinium halide. The hydrazinium salts in the tetrahydro- and hexahydrophthalimido series are prepared in the same manner.

To obtain the active phthalimido ester having the formula:

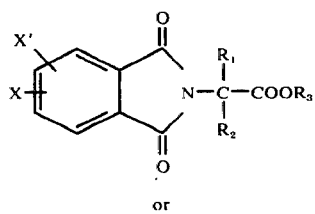

or

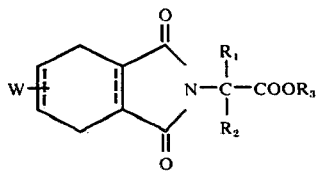

where W,X,X', $R_1$, $R_2$ and ------ are as defined above, and $R_3$ is alkyl $C_1$–$C_4$, the corresponding acid, i.e. where $R_3$ is hydrogen, is treated with a diazoalkane $C_1$–$C_4$ in the presence of a solvent, such as an ether.

presence of an acid acceptor, such as pyridine, triethylamine, sodium bicarbonate, and the like.

The phthalimido nitrile can be obtained by dehydration of the corresponding amide using titanium tetrachloride, phosphorus pentoxide, phosphorus oxychoride, acetic anhydride, trifluoroacetic anhydride, or the like, in the presence of a solvent, such as benzene, tetrahydrofuran, or the like. This reaction can be carried out at a temperature between about 0° C. and 100° C.

Alternatively, these compounds can be prepared by reacting a compound of the formula:

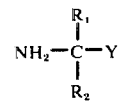

where $R_1$, $R_2$ and Y are as indicated above, with the exception that Y cannot be —$COR_7$ or —CONHN $^+(R_6)_3$ halide $^-$, with a substituted phthaloyl chloride of the formula:

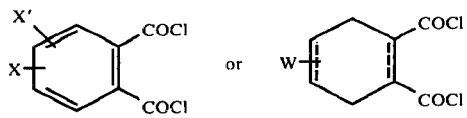

where W, X and X' are as indicated above.

Alternatively, these compounds can be prepared by reacting the compound:

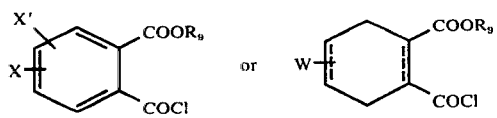

where W, X and X' are as defined above and $R_9$ is alkyl $C_1$–$C_4$ with a compound of the formula:

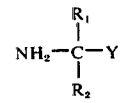

where $R_1$, $R_2$ and Y are as indicated above, except that Y cannot be —$COR_7$ or —CONHN $^+(R_6)_3$ halide $^-$, to give a product:

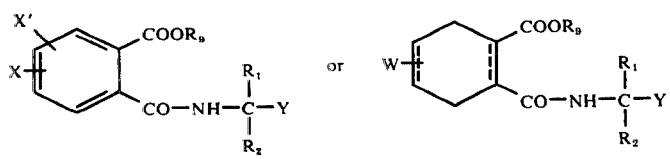

This reaction can be carried out at a temperature between about —10° C. and +30° C.

Alternatively, the appropriate α-amino ester can be allowed to react with the appropriate phthalic tetrahydrophthalic or hexahydrophthalic anhydride to afford the phthalamido, tetrahydrophthalimido or hexahydrophthalimido ester, or the acid halide, prepared as above, may be treated with a lower $C_1$–$C_4$ alkanol in the which can then be cyclized to give product:

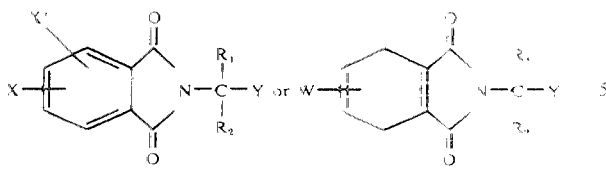

where W, X, X', $R_1$, $R_2$ and Y are as indicated above, except that Y cannot be —$COR_7$ or —$CONHN^+(R_6)_3$ . halide⁻.

The plant growth regulating effects obtained with compounds having the structure:

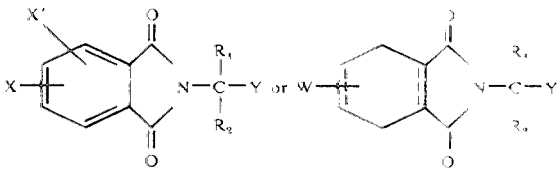

where W is hydrogen or lower alkyl $C_1$-$C_4$; X and X' are hydrogen, alkyl $C_1$-$C_4$, halogen, alkanoylamino $C_1$-$C_4$ $CF_3$, alkoxy $C_1$-$C_4$, benzyloxy, di($C_1$-$C_4$) alkylamino, $C_1$-$C_4$ alkylthio, hydroxy, $C_1$-$C_4$ alkylsulfonyl, or nitro; Y is —$COOR_3$, —$CONHR_8$, —$CONR_3R_4$, —$CONH(R_5)_2$, —$CONHN^+(R_6)_3$ . halide⁻ or —CN; $R_1$ and $R_2$ each represent alkyl $C_1$-$C_4$, or when taken together form cycloalkyl $C_4$-$C_{11}$ optionally substituted with methyl; $R_3$ and $R_4$ each represent hydrogen or alkyl $C_1$-$C_4$; and $R_5$ and $R_6$ each represent alkyl $C_1$-$C_2$, and $R_8$ is —$CH_3$ or

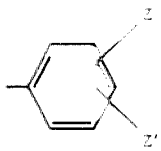

where Z and Z' are hydrogen, halogen, alkyl $C_1$-$C_2$, $CF_3$ or —$OCH_3$, are widely varied and most remarkable.

One very surprising aspect of this invention is the finding that virtually every plant species tested in accordance with the invention responded, rather dramatically, in a very desirable manner regardless of the method of application employed or the specific compound or formulation used.

Another very surprising aspect of the invention is the finding that although the plant growth regulating effects of the compounds within the generic class described above sometimes varies from plant to plant and specific compound to specific compound, all compounds are highly active at low rates of application and none appear to be phytotoxic even when applied at rates as high as 32 pounds per acre in the treated area. In practice, it will, therefore, generally be found desirable to employ from about 0.06 pound to 32 pounds per acre, and preferably 0.06 pound to 4.0 pounds per acre of the active phthalimido compound in the treated area to obtain the desired plant growth regulant effect.

Among the desired effects obtained with the compounds of the invention are:

A. Increased internode growth evidenced by longer internodes having increased dry weight;
B. Increased leaf size evidenced by increased dry weight;
C. Induced flowering and/or bolting in certain varieties of plants;
D. Increased set in tuberous plants;
E. Increased rate of seedling emergence and increased height of seedling plants; and
F. Delay of senescence, especially in flowering plants;
G. Causes fruit clusters, e.g. grapes, to open or spread reducing the liklihood of fungal attack.

The advantages obtained with increased internode length are multiple. They include, in addition to a general increase in the total size and weight of the plant, opening or spreading of plant leaves which generally makes the plant less vulnerable to disease through better ventilation. Moreover, increased internode length has particular advantage for crops, such as soybeans, cotton, tobacco, sugar cane, timber and seed corn. With soybeans it has been found that the lower pods, normally lost at harvest because they are below the level of the harvesting elements, are now sufficiently elevated by the elongation of the plant internodes to be harvested. This mechanism thus increases soybean yields a significant 3 to 4 bushels per acre and facilitates more rapid harvest. Similarly, elongation of cotton and tobacco internodes elevates the lower cotton bolls and lower tobacco leaves sufficiently to prevent their normal destruction or damage by the elements (i.e. abrasion, disease, etc.).

With sugar cane and timber, longer internodes produce larger cane and trees resulting in greater yields of sugar and lumber, whereas, longer internodes in seed corn raises the corn tassel, i.e. the male organ of the plant, high enough that it can be removed from all plants in a field with a single cutting before pollination occurs. Controlled pollination, to provided a desired hybird corn, can then be effected at will.

The advantage of increasing the leaf size of plants is obvious and of particular importance for those plants wherein the leaves constitute the marketable crop. Tobacco, forage crops and leafy vegetables, such as spinach, swiss chard, lettuce and cabbage, exemplify such crops.

Accelerated flowering and bolting is important for crops which are grown for seed. Among the important crops of this type are lettuce, radish, sugar beets, red beets, brussel sprouts, broccoli and carrots.

Increased set in tuberous plants, such as potatoes, is another important advantage of this invention, since the treated plants develop two to three times as many potatoes as the untreated plants. Moreover, the potatoes on treated plants are vastly more uniform than those on untreated plants, although they are only average in size. This, however, is an advantage where the potatoes are to be used for canning.

Enhancement of the rate of seedling emergence and increased height of seedling plants are still other advantages obtained with the compounds of this invention. In certain regions, for example, the Mississippi Delta in the United States, soil structure and moisture content can present serious problems for the farmer. In order to assure germination of plants in this region, it is sometimes necessary to plant rather deeply. If the plants emerge before a heavy rain, they usually mature normally. However, when heavy rains occur between planting and emergence, it is not an uncommon occurrence to find that a crusting of the soil surface takes place. Seeds which have not emerged by this time cannot break the crust and generally rot in the ground. Thus, the only recourse to the farmer is to replant.

It would, therefore, be most advantageous if a compound could be found which would hasten germination and enhance the growth rate of seedling plants.

A still further advantageous effect obtained with the compounds of the present invention is the delay of senescence in plants. This effect is especially important to nursery men and florists who desire to extend the life of the blooms in flowering plants.

Surprisingly, we have discovered that the phthalimido compounds described above, particularly the halo-substituted phthalimidocycloalkylcarboxamides, provide these advantages.

We have also found that the effectiveness of the compounds of the invention as plant growth regulating agents is not limited by formulation or method of application. The active compounds may be formulated as dusts, dust concentrates, wettable powders, emulsifiable concentrates, soil drenches, granular formulations, and the like. They may be applied in combination with a solid or liquid diluent by a variety of methods, including: root dips, seed coatings, trans plant water, foliar application, preplant incorporation in the soil, preemergence soil application, and low volume application in the form of discrete droplets having a mass median diameter of from 25 to 150 microns.

Typical formulations which are useful in the practice of the present invention include: wettable powders, dusts dust concentrates, granular formulations and flowable formulations.

Wettable powders can be prepared by blending the active phthalimide derivative with a solid carrier, such as attapulgite, kaolin, diatomaceous earth, silica, or the like, and a small amount of a dispersant and wetting agent and air- milling the blended mixture to effect reduction of particle size to about the 5 to 10 micron range. A typical wettable powder might contain 50% by weight of the phthalimide derivative, 5% by weight of a highly purified partially desulfonated sodium lignin sulfonate, 1% by weight of sodium N- methyl-N-oleoyl-taurate and 44% by weight of attapulgite.

In practice, it will also be found that the active ingredient in the above formulation can be varied from about 25% to 80% by weight. However, in such cases, the solid diluent will have to be varied accordingly.

For the preparation of a dust, for example a 10% dust, 20% by weight of the 50% wettable powder can be blended with about 80% by weight of a solid carrier, such as kaolin. Suitable equipment for such preparations are ribbon-type blenders and double-cone blenders. It is also obvious that the concentration of active ingredient in dust formulations can be readily varied by adjusting the amount of wettable powder and carrier used. Typical dusts will generally vary between about 1% to 15% by weight of active ingredient, although higher concentrations may also be prepared.

An alternative process for preparation of dusts, also dust concentrates, involves blending the active phthalimide derivative with the solid carrier and passing the uniform blend through an attrition mill to obtain the desired particle size.

A typical granular formulation can be prepared by blending a small amount, i.e. about 0.3% by weight, of a fumed colloidal silica with about 5.6% by weight of the phthalimido derivative and air-milling the mixture to a uniform blend. Silica sand, about 85,7% weight, is then placed in a blender along with about 0.7% by weight of calcium-sodium lignin sulfonate powder and 4.2% of a 1% aqueous solution of calcium-sodium lignin sulfonate. The mixture is blended and then 3.5% by weight of synthetic calcium silicate is added. The mixture is permitted to continue blending for several minutes until the finished product is uniformly coated and free flowing. It is, of course, obvious that the amount of active ingredient in the formulated granular product can be widely varied, preferably between about 1% to 15% by weight. This simply requires appropriate adjustments of the amount of granular carrier used and/or adjuvants added. It is likewise obvious that sorptive granular carriers, as well as nonsorptive carriers, can be employed in the preparation of the granular formulation.

Other formulations, methods, products and advantages of the present invention may become apparent from the examples set forth below. These examples are provided simply as an illustration of the invention and are not intended to be limiting thereon.

EXAMPLE 1

Preparation of
1-(3-Chlorophthalimido)cyclohexanecarboxylic Acid

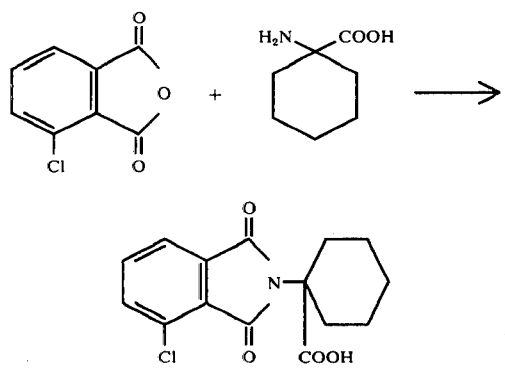

Method A

A mixture containing 1 kg. 1-aminocyclohexanecarboxylic acid, 1.275 kg. 3-chlorophthalic anhydride and 91 ml. triethylamine in 6.3 liters toluene is stirred and heated under reflux under a Dean-Stark water separator for 20 hours. During this time, 154 ml. of water are collected. The solution is cooled to 0° C. to 5° C., and the product then collected by filtration in a yield of 77%. This material has melting point 193° C. to 194° C.

Method B

An intimate mixture of 4.56 grams 3-chlorophthalic anhydride and 3.58 grams 1-aminocyclohexanecarboxylic acid is heated at 210° C. until no more water vapor is evolved. The cooled mixture is dissolved as far as possible in boiling acetone, and the insolubles removed by filtration. The acetone is removed from the filtrate and the crystalline residue transferred to a filter funnel with ether and air dried. The product is identical to that described in Method A above.

Method C.

A mixture containing 91.3 grams 3-chlorophthalic anhydride and 71.6 grams 1-aminocyclohexanecarboxylic acid in one liter acetic acid is heated under reflux for 21 hours. The solvent is then removed under reduced pressure, 250 ml. toluene added to the residue and the solvent again removed in vacuo. The residue is heated in one liter acetone and the insolubles removed by filtration. The solvent is removed by distillation, and the residue transferred to a filter funnel with ether and air dried. The product is identical to that prepared in Method A above.

Method D

A mixture containing 9.13 grams 3-chlorophthalic anhydride and 7.16 grams 1-aminocyclohexanecarboxylic acid in 100 ml. dimethylformamide is heated under reflux for 24 hours. The mixture is cooled, poured into ice water and the precipitated solid removed by filtration, washed with water and air dried. Recrystallization of the solid from 95% ethanol with filtration to remove insolubles gives the product identical to that prepared by Method A.

The phthalimido acids of Table I, below, are prepared by the general methods described above.

EXAMPLE 2

Preparation of 1-(3-Chlorophthalimido)cyclohexanecarbonyl Chloride

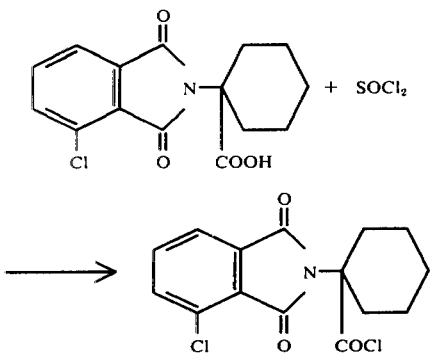

In a 12 liter flask is placed 1.5 kg. of the 1-(3-chlorophthalimido)cyclohexanecarboxylic acid and 7500 ml. benzene. The mixture is stirred and heated to boiling, and then 696 grams thionyl chloride added

TABLE I

| X | X' | $R_1$ | $R_2$ | Solvent | Method | Melting Point °C. |
|---|---|---|---|---|---|---|
| 3-$NO_2$ | H | $CH_3$ | $-CH_2CH(CH_3)_2$ | Xylene | A | 90.5–92 |
| 3-$NO_2$ | H |  | $-(CH_2)_5-$ |  | A, B, C | 178–179 |
| H | H |  | $-(CH_2)_4-$ |  | B | 156–157 |
| H | H |  | $-(CH_2)_5-$ | Toluene | A | 174.5–176 |
| 3-Cl | H | $CH_3$ | $-CH(CH_3)_2$ | — | B | 162–164 |
| 3-Cl | H |  | $-(CH_2)_6-$ | — | B | 188–189.5 |
| 3-Cl | H |  | $-(CH_2)_4-$ | — | B | 182–185 |
| 3-$CH_3$ | H |  | $-(CH_2)_6-$ | — | B | 168–169 |
| 4-$CH_3$ | H |  | $-(CH_2)_5-$ | Toluene | A | 167–168 |
| 4-Cl | H |  | $-(CH_2)_5-$ | — | B | 184–185 |
| 4-Cl | H |  | $-(CH_2)_4-$ | — | B | 166–167.5 |
| 3-I | H |  | $-(CH_2)_5-$ | — | B | 191–192 |
| 3-F | H |  | $-(CH_2)_5-$ | — | A, B | 160–164 |
| 3-Cl | H | $CH_3$ | $-CH_2CH(CH_3)_2$ | — | B | oil |
| 4-$CH_3$ | H |  | $-(CH_2)_4-$ | — | B | 156.5–157 |
| 3-$CH_3$ | H |  | $-(CH_2)_4-$ | — | B | 150.5–151 |
| 3-$CH_3$ | H |  | $-(CH_2)_5-$ | Toluene | A | 176–177 |
| 4-Cl | H |  | $-(CH_2)_7-$ | Toluene | A | 189–191 |
| 3-Br | H |  | $-(CH_2)_5-$ | Toluene | A | 197–198.5 |
| 4-Cl | H | $CH_3$ | $-CH(CH_3)_2$ | — | B | 184–185.5 |
| 3-Cl | H |  | $-CH_2-CH(CH_3)-CH_2-CH_2-CH_2-$ | Toluene | A | oil |
| 3-$CH_3$ | H |  | $-CH_2-CH(CH_3)-CH_2-CH_2-CH_2-$ | Toluene | A | 150–152 |
| 3-NHCOCH$_3$ | H |  | $-(CH_2)_5-$ | Toluene | A | 214.5–216.5 |
| 3-Br | 4-Br |  | $-(CH_2)_5-$ | Xylene | A | 210–212 |
| 4-OCH$_3$ | H |  | $-(CH_2)_5-$ | Xylene | A | 136–138 |
| 3-Cl | 5-Cl |  | $-(CH_2)_5-$ | Xylene | A | 102–105 |
| 3-Cl | 6-Cl |  | $-(CH_2)_5-$ | Xylene | A | 183–184 |
| 3-OC$_2$H$_5$ | 6-OC$_2$H$_5$ |  | $-(CH_2)_5-$ | Xylene | A | 187–192 |
| 4-CH$_3$ | 5-CH$_3$ |  | $-(CH_2)_5-$ | Xylene | A | 209–219 |
| 4-OCH$_2$C$_6$H$_5$ | H |  | $-(CH_2)_5-$ | Xylene | A | 210–218 |
| 3-CF$_3$ | H |  | $-(CH_2)_5-$ | Toluene | A | oil |
| 3-N(CH$_3$)$_2$ | H |  | $-(CH_2)_5-$ | Xylene | A | 143–149.5 |
| 3-CH$_3$ | 6-CH$_3$ |  | $-(CH_2)_5-$ | Xylene | A | 179–182 |
| 3-OC$_2$H$_5$ | 5-OC$_2$H$_5$ |  | $-(CH_2)_5-$ | — | B | 196–202.5 |
| 3-OCH$_2$C$_6$H$_5$ | 6-CH$_3$ |  | $-(CH_2)_5-$ | Xylene | A | 203–203.5 |
| 3-SCH$_3$ | H |  | $-(CH_2)_5-$ | Xylene | A | 204–205 |
| 3-CCl$_3$ | H |  | $-(CH_2)_5-$ | Toluene | A | 201–205 |
| 3-SC$_2$H$_5$ | 6-CH$_3$ |  | $-(CH_2)_5-$ | — | B | 163–163.5 | dropwise. After the addition, heating is continued for 2 hours. The volume of the solution is reduced by one-half, the solution filtered, and the remaining solvent removed under reduced pressure. The acid chloride is used for the preparation of the carboxamides without further purification.

Using the procedure described above, the following acid chlorides are prepared from the corresponding acids described in Table II. These acid chlorides are used directly without further purification and are characterized only by their infrared spectrum.

TABLE II

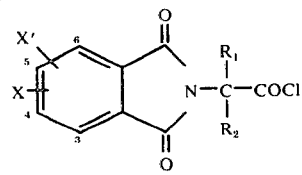

| X | X' | R₁ | R₂ |
|---|---|---|---|
| 3-NO₂ | H | | —(CH₂)₅— |
| H | H | | —(CH₂)₄— |
| H | H | | —(CH₂)₅— |
| 3-Cl | H | CH₃ | —CH(CH₃)₂ |
| 3-Cl | H | | —(CH₂)₆— |
| 3-Cl | H | | —(CH₂)₄— |
| 3-CH₃ | H | | —(CH₂)₆— |
| 4-CH₃ | H | | —(CH₂)₅— |
| 4-Cl | H | | —(CH₂)₅— |
| 4-Cl | H | | —(CH₂)₄— |
| 3-I | H | | —(CH₂)₅— |
| 3-F | H | | —(CH₂)₅— |
| 3-Cl | H | CH₃ | —CH₂CH(CH₃)₂ |
| 4-CH₃ | H | | —(CH₂)₄— |
| 3-CH₃ | H | | —(CH₂)₄— |
| 3-CH₃ | H | | —(CH₂)₅— |
| 4-Cl | H | | —(CH₂)₇— |
| 3-Br | H | | —(CH₂)₅— |
| 4-Cl | H | CH₃ | —CH(CH₃)₂ |
| 3-Cl | H | | —CH₂CH(CH₃)—CH₂—CH₂—CH₂— with CH₃ branch |
| 3-CH₃ | H | | —CH₂—CH(CH₃)—CH₂—CH₂—CH₂— |
| 3-NHOOCH₃ | H | | —(CH₂)₅— |
| 3-Br | 4-Br | | —(CH₂)₅— |
| 4-OCH₃ | H | | —(CH₂)₅— |
| 3-Cl | 5-Cl | | —(CH₂)₅— |
| 3-Cl | 6-Cl | | —(CH₂)₅— |
| 3-OC₂H₅ | 6-OC₂H₅ | | —(CH₂)₅— |
| 4-CH₃ | 5-CH₃ | | —(CH₂)₅— |
| 4-OCH₂C₆H₅ | H | | —(CH₂)₅— |
| 3-CF₃ | H | | —(CH₂)₅— |
| 3-N(CH₃)₂ | H | | —(CH₂)₅— |
| 3-CH₃ | 6-CH₃ | | —(CH₂)₅— |
| 3-OC₂H₅ | 5-OC₂H₅ | | —(CH₂)₅— |
| 3-OCH₂C₆H₅ | 6-CH₃ | | —(CH₂)₅— |
| 3-SCH₃ | H | | —(CH₂)₅— |

TABLE II-continued

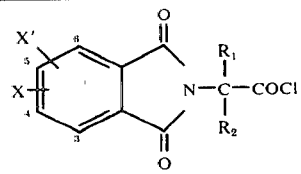

| X | X' | R₁ | R₂ |
|---|---|---|---|
| 3-SC₂H₅ | 6-CH₃ | | —(CH₂)₅— |
| 3-CCl₃ | H | | —(CH₂)₅— |
| 3-SC₂H₅ | 6-CH₃ | | —(CH₂)₅— |

EXAMPLE 3

Preparation of 1-(3-Chlorophthalimido)cyclohexanecarboxamide

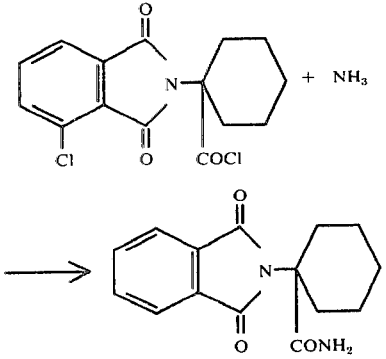

A solution containing the crude acid chloride prepared in Example 2 is dissolved in 8 liters of tetrahydrofuran and cooled to 10° C. to 15° C. Gaseous ammonia is bubbled through the stirred solution until an excess of ammonia begins escaping from the reaction flask. The mixture is stirred for a further 15 minutes and then filtered. The solids are washed with water thoroughly to remove inorganic salts and the product is air dried. The tetrahydrofuran filtrate is evaporated under reduced pressure, and the residue combined with the air-dried solid and heated to boiling in 3 liters toluene, cooled to 10° C. and the product removed by filtration to give 1.2 kg. product, melting point 194° C. to 195° C.

The carboxamides of Table III, below, are prepared by essentially the same procedure as described above.

TABLE III

| X | X' | R₁ | R₂ | Melting Point ° C. |
|---|---|---|---|---|
| 3-Cl | H | | —(CH₂)₄— | 175–177 |
| 3-Cl | H | | —(CH₂)₆— | 163–164 |
| H | H | | —(CH₂)₄— | 218.5–220 |
| 3-NO₂ | H | | —(CH₂)₅— | 189.5–190.5 |
| H | H | | —(CH₂)₅— | 224–226 |
| 3-Cl | H | CH₃ | —CH(CH₃)₂ | 137–138 |
| 3-Cl | H | CH₃ | —CH₂CH(CH₃)₂ | 161–162 |
| 3-CH₃ | H | | —(CH₂)₆— | 187.5–189 |
| 4-Cl | H | | —(CH₂)₄— | 177–178 |
| 4-CH₃ | H | | —(CH₂)₅— | 170.5–180 |
| 3-F | H | | —(CH₂)₅— | 207–208 |

TABLE III-continued

| X | X' | $R_1$ | $R_2$ | Melting Point °C |
|---|----|-------|-------|------------------|
| 3-I | H | | $-(CH_2)_5-$ | 222–223 |
| 4-Cl | H | | $-(CH_2)_5-$ | 188.5–190 |
| 4-$CH_3$ | H | | $-(CH_2)_4-$ | 182–183 |
| 3-$CH_3$ | H | | $-(CH_2)_4-$ | 172–173 |
| 3-$CH_3$ | H | | $-(CH_2)_5-$ | 185–186.5 |
| 4-Cl | H | | $-(CH_2)_7-$ | 159–161 |
| 3-Br | H | | $-(CH_2)_5-$ | 199–200 |
| 4-Cl | H | $-CH_3$ | $-CH(CH_3)_2$ | 173–174 |
| 3-Cl | H | | $-CH_2-\underset{CH_3}{\overset{CH_3}{\overset{|}{C}H}}-CH_2-CH_2-CH_2-$ | 195–196 |
| 3-$CH_3$ | H | | $-CH_2-\underset{CH_3}{\overset{|}{C}H}-CH_2-CH_2-CH_2-$ | 165–167 |
| 3-NHCOCH$_3$ | H | | $-(CH_2)_5-$ | 181.5–182.5 |
| 3-Br | 4-Br | | $-(CH_2)_5-$ | 185.5–187 |
| 4-OCH$_3$ | H | | $-(CH_2)_5-$ | 158–159 |
| 3-Cl | 5-Cl | | $-(CH_2)_5-$ | 166–167 |
| 3-Cl | 6-Cl | | $-(CH_2)_5-$ | 216.5–218 |
| 3-OC$_2$H$_5$ | 6-OC$_2$H$_5$ | | $-(CH_2)_5-$ | 213.5–217.5 |
| 4-CH$_3$ | 5-CH$_3$ | | $-(CH_2)_5-$ | 198–200.5 |
| 4-OCH$_2$C$_6$H$_5$ | H | | $-(CH_2)_5-$ | 170–171.5 |
| 3-CF$_3$ | H | | $-(CH_2)_5-$ | 166–167 |
| 3-N(CH$_3$)$_2$ | H | | $-(CH_2)_5-$ | 166.5–169 |
| 3-CH$_3$ | 6-CH$_3$ | | $-(CH_2)_5-$ | 191–193.5 |
| 3-OC$_2$H$_5$ | 5-OC$_2$H$_5$ | | $-(CH_2)_5-$ | 172–173.5 |
| 3-OCH$_2$C$_6$H$_5$ | 6-CH$_3$ | | $-(CH_2)_5-$ | 191–192 |
| 3-SCH$_3$ | H | | $-(CH_2)_5-$ | 212–213 |
| 3-SO$_2$C$_2$H$_5$ | 6-CH$_3$ | | $-(CH_2)_5-$ | 202–203 |
| 3-CCl$_3$ | H | | $-(CH_2)_5-$ | 193–195.5 |

EXAMPLE 4

Preparation of 1-(3-chlorophthalimido)-N,N-dimethylcyclohexanecarboxamide

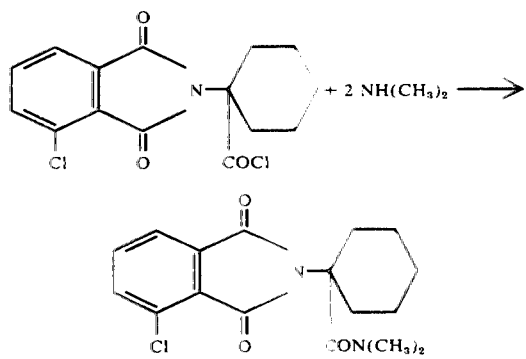

A solution containing 7.43 grams 1-(3-chlorophthalimido)cyclohexanecarbonyl chloride in 50 ml. tetrahydrofuran is cooled to 10° C. to 15° C., and while stirring, gaseous dimethylamine is bubbled into the solution until saturated. After a further 5 minutes, the mixture is filtered to remove salts and the solvent removed from the filtrate. The residue is crystallized from cyclohexane to give the product, melting point 135° C. to 137° C.

The N,N-dimethylcarboxamides of Table IV, below, are prepared using essentially the same procedure described above.

TABLE IV

| X | X' | $R_1$ | $R_2$ | $R_3$ | $R_4$ | Melting Point °C |
|---|----|-------|-------|-------|-------|------------------|
| H | H | $-(CH_2)_5-$ | | $CH_3$ | $CH_3$ | 112–113 |
| 3-$NO_2$ | H | $-(CH_2)_5-$ | | $CH_3$ | $CH_3$ | 132.5–134.5 |

EXAMPLE 5

Preparation of 1-(3-Chlorophthalimido)cyclohexanecarboxylic Acid, 2,2-Dimethylhydrazide

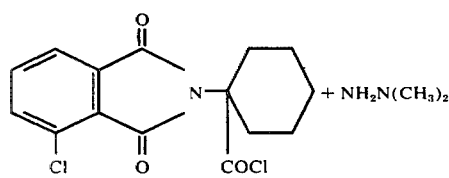

-continued

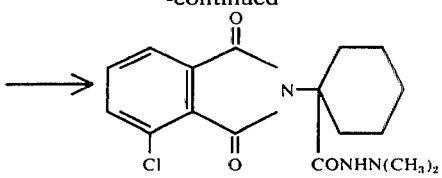

To an ice-cold solution of acid chloride in tetrahydrofuran is added dropwise two equivalents of 1,1-dimethylhydrazine. After stirring a further 0.5 hour, the solids are removed by filtration and the solvent removed in vacuo from the filtrate. The residue is crystallized from acetonitrile to give the product, melting point 184° C. to 185° C.

EXAMPLE 6

Preparation of
2-[1-(3-Chlorophthalimido)cyclohexylcarbonyl]-1,1,1-trimethylhydrazinium Chloride.

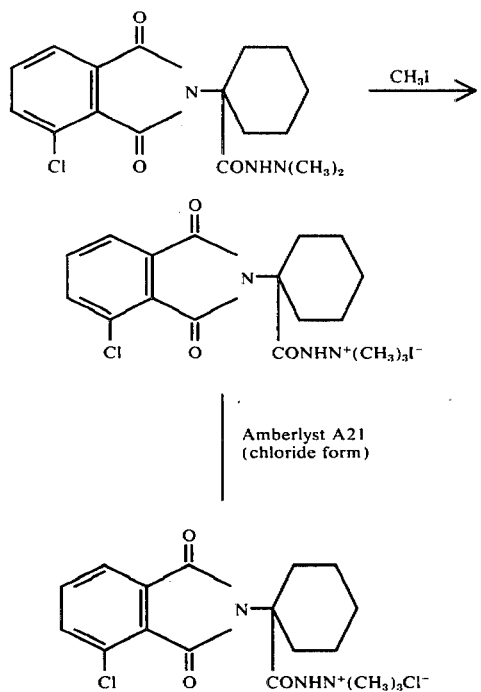

To the dimethylhydrazide prepared as described in Example 5 in tetrahydrofuran is added excess methyl iodide and the mixture heated under reflux for 4 hours. The solids are removed by filtration and air dried to give the quaternary iodide. The iodide is converted to the chloride by passing a 50% aqueous ethanol solution of the salt slowly down a column packed with Amberlyst A21, an organic ion exchange resin, in its chloride form and evaporating the eluent. The residue is crystallized from ethanol-ether to give the chloride salt, melting point 202° C. to 203° C.

EXAMPLE 7

Preparation of Ethyl and Methyl 1-(3-chlorophthalimido)cyclohexanecarboxylate

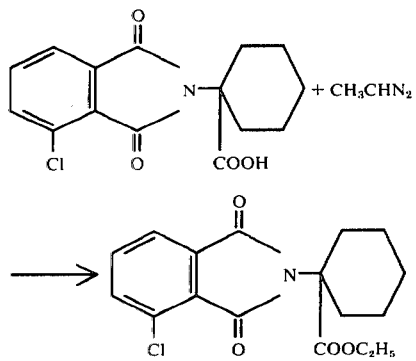

An excess of an ether solution of diazoethane is added to a solution of 1-(3-chlorophthalamido)cyclohexanecarboxylic acid in tetrahydrofuran. After standing for 1 hour at room temperature, the solution is washed with excess aqueous sodium carbonate solution, followed by two water washes. The organic phase is dried and the solvent evaporated under reduced pressure. The residue is crystallized from hexane to give the ester, melting point 70° C. to 71° C.

Alternatively, this ester can be prepared by the action of ethanol and pyridine on the acid chloride, described in Example 2.

Methyl 1-(3-chlorophthalamido)cyclohexanecarboxylate is prepared by heating 5.7 g. or 3-chlorophthalic anhydried with 4.9 g. methyl 1-aminocyclohexanecarboxylate in 100 ml. of toluene containing 2 ml. triethylamine under a Dean-Stark separator for 24 hours. The solvent is removed under reduced pressure and the residue dissolved as far as possible in ether. The product crystallized from a mixture of ether and hexane to give 5.7 g. methyl ester, m.p. 90°–92° C.

EXAMPLE 8

Preparation of
α-(3-Chlorophthalimido)-α-isoproyl-α-methylacetonitrile

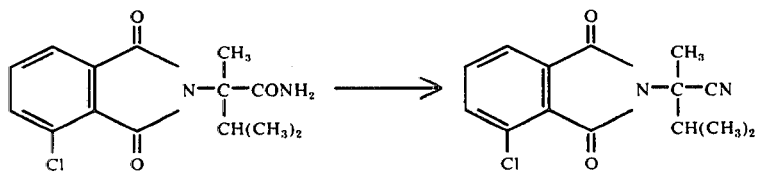

To 60 ml. dry tetrahydrofuran, stirred and cooled to 0° C. is added dropwise 11.5 ml. titanium tetrachloride in 15 ml. dry carbon tetrachloride. To this cold mixture is added 8.82 grams of α-(3-chlorophthalimido)-α-isopropyl-α-methylacetamide in 50 ml. dry tetrahydrofuran, followed by 12.3 grams triethylamine in 20 ml. dry tetrahydrofuran. The reaction mixture is allowed to warm slowly to room temperature and kept overnight. Water is then added cautiously to the mixture while it is extracted three times with ether. The combined extracts are washed with water, dried, and evaporated. The residue is crystallized from ether-hexane to give 6.1 grams of the nitrile, melting point 71° C. to 72° C.

The starting amide can be dehydrated by other reagents, such as phosphorus pentoxide and phosphorus oxychloride in benzene, acetic anhydride and trifluoroacetic anhydride to yield the same product.

EXAMPLE 9

Preparation of 2,2-Disubstituted-2-(3,4,5,6-tetrahydrophthalimido)acetic acids

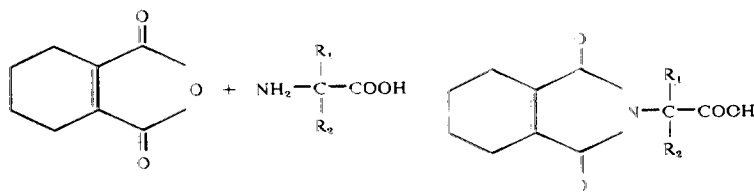

Using the procedure set forth in Example 1 but substituting 3,4,5,6-tetrahydrophthalic anhydride for 3-chlorophthalic anhydride affords the compounds set forth in Table V.

TABLE V

| $R_1$ | $R_2$ | Solvent | Method | Melting Point |
|---|---|---|---|---|
| | —(CH$_2$)$_5$— | Xylene | A | 134–136° |
| | —(CH$_2$)$_4$— | Xylene | A | 86–87° |
| | —(CH$_2$)$_6$— | Xylene | A | Oil |
| CH$_3$ | —CH$_2$CH(CH$_3$)$_2$ | Xylene | A | 118–119.5° |
| CH$_3$ | —CH(CH$_3$)$_2$ | Xylene | A | Oil |

EXAMPLE 10

Preparation of 2,2-Disubstituted-2-(3,4,5,6-tetrahydrophthalimido)acetyl chloride Using the procedure set forth in Example 2 but substituting the acids listed in Table V and Example 9 for 1-(3-chlorophthalimido) cyclohexanecarboxylic acid, the acid chlorides listed in Table VI are prepared. These acid chlorides are obtained as oils and used directly without further purification and are characterized only by their infrared spectra.

TABLE VI

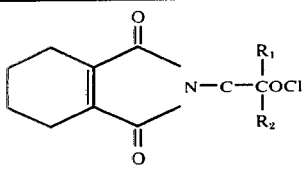

| $R_1$ | $R_2$ |
|---|---|
| | —(CH$_2$)$_5$— |
| | —(CH$_2$)$_4$— |
| | —(CH$_2$)$_6$— |
| CH$_3$ | CH$_2$CH(CH$_3$)$_2$ |

TABLE VI-continued

| $R_1$ | $R_2$ |
|---|---|
| CH$_3$ | CH(CH$_3$)$_2$ |

EXAMPLE 11

Preparation of 2,2-Disubstituted-2-(3,4,5,6-tetrahydrophthalimido)acetamides

Using the procedure set forth in Example 3 but substituting the acid chlorides listed in Table VI for 1-(3-chlorophthalimido)cyclohexanecarbonyl chlorides, the amides listed in Table VII are prepared.

Table VII

| $R_1$ | $R_2$ | Melting Point ° C |
|---|---|---|
| | —(CH$_2$)$_5$— | 203–204 |
| | —(CH$_2$)$_4$— | 172–173 |
| | —(CH$_2$)$_6$— | 133–134 |
| CH$_3$ | —CH$_2$CH(CH$_3$)$_2$ | 129–130 |
| CH$_3$ | —CH(CH$_3$)$_2$ | 142.5–143.5 |

EXAMPLE 12

Preparation of 1-(1,2,3,6-Tetrahydrophthalimido)-1-cyclohexanecarboxylic acid

Using the procedure set forth in Example 1 but substituting 1,2,3,6-tetrahydrophthalic anhydride for 3-chlorophthalic anhydride, the following compound is prepared.

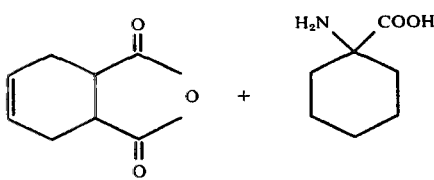

Method A

-continued

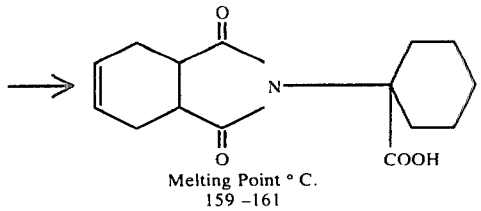

Melting Point ° C.
159 –161

EXAMPLE 13

Preparation of 1-(1,2,3,6-Tetrahydrophthalimido)-1-cyclohexanecarbonyl chloride

Using the procedure set forth in Example 2 but substituting the acid of Example 12 for 1-(3-chlorophthalimido)cyclohexanecarboxylic acid, the acid chloride shown below is prepared. This acid chloride is used directly without further purification and is characterized only by the infrared spectra.

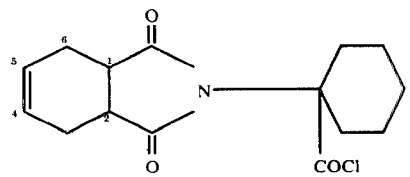

EXAMPLE 14

Preparation of 1-(1,2,3,6-Tetrahydrophthalimido)-1-cyclohexanecarboxamide

Using the procedure set forth in Example 3 but substituting the acid chloride from Example 13 for 1-(3-chlorophthalimido) cyclohexanecarbonyl chloride, gives the amide listed below.

TABLE VIII

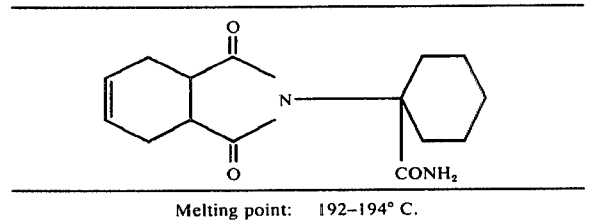

Melting point: 192–194° C.

EXAMPLE 15

Preparation of Methyl 1-(3,4,5,6-tetrahydrophthalimido)-1-cyclohexanecarboxylate

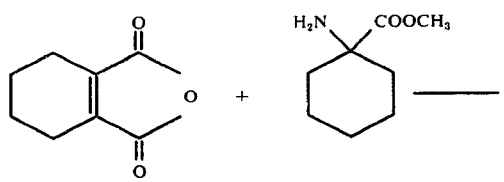

-continued

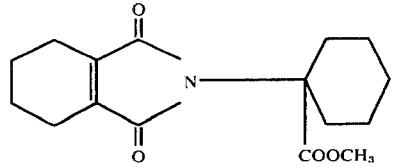

A mixture containing 11.4 g 1-cyclohexene-1,2-dicarboxylic acid anhydride, 11.8 methyl 1-aminocyclohexanecarboxylate and triethylamine in 150 ml. toluene was heated under reflux under a Dean-Stark water trap overnight. Removel of the solvent left an oil which was purifed by chromatography on magnesium silicate to give the crystalline, ester, m.p. 44°–45° C.

EXAMPLE 16

Preparation of 1-(3,4,5,6-Tetrahydropthalimido)-1-cyclohexanecarbonitrile

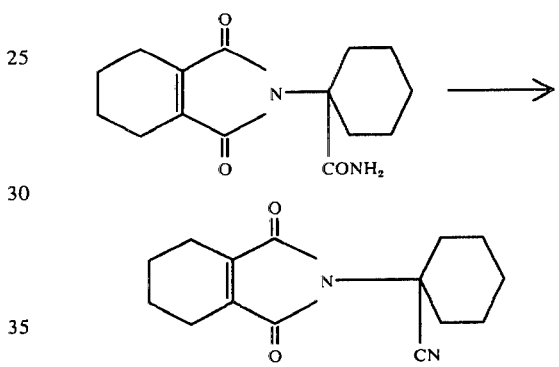

Using the procedure described in Example 8 but substituting 1-(3,4,5,6-tetrahydroophthalimido)-1-cyclohexanecarboxamide for α-(3-chlorophthalimido)-α-isoproply-α-methylacetamide, the title compound if formed, m.p. 55.5°–56.5° C.

EXAMPLE 17

Preparation of 1-(3-chlorophthalimido)-N-methyl-1-cyclohexanecarboxamide

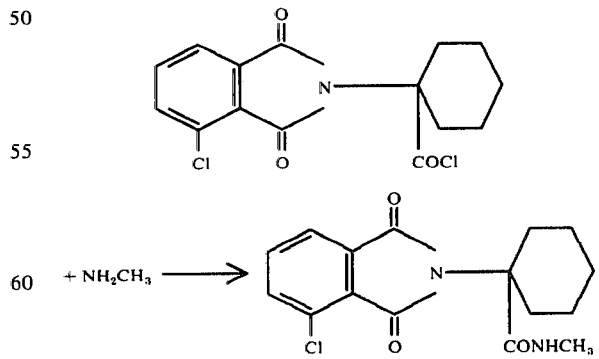

Using the same procedure of described in Example 3 but replacing the ammonia with methylamine gives the title mono-methylamide, m.p. 168.5–170° C. Similarly, receiving 1-(3-acetamidophthalimide)-cyclohexanecarbonyl chloride with methylamine yields 1-(3-acetamidophthalimido)-N-methylcyclohexanecarboxamide, m.p. 205°–207.5° C.

EXAMPLE 18

Preparation of 4'-Chloro-1-(3-methylphthalimido)-1-cyclohexanecarboxanilide

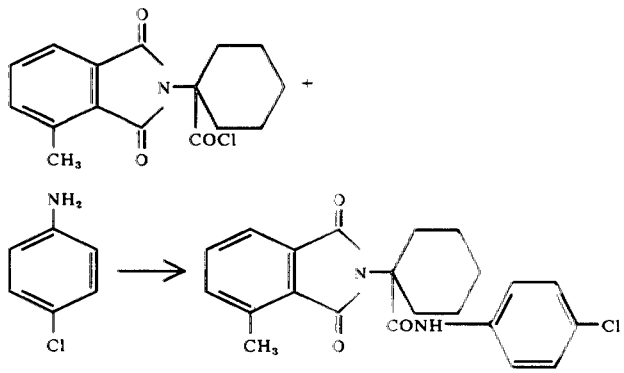

To a solution containing 13.16 g. of the acid chloride described in Table II in 125 ml. tetrahydroduran was added dropwise with stirring at room temperature a solution containing 11.0 g. p-chloroaniline in 75 ml. tetrahydrofuran. After a further 0.5 hour, the mixture was filtered, the filtrate evaporated and the residue crystallized from acetonitrile to give the desired carboxanilide m.p. 208.5°–209° C.

EXAMPLE 19

Preparation of 1-(hexahydrophthalimido)cyclohexanecarboxylic acids.

Using the procedure described in Example 1 but substituting cyclohexane-1,2-dicarboxylic anhydride and 4-methylcylohexane-1,2-dicarboxylic anhydride for 3-chlorophthalic anhydride, the hexahydrophthalimido compounds in Table IX are prepared.

Table IX

| W | Solvent | Method | Melting Point ° C. |
|---|---|---|---|
| H | Toluene | A | 135–136 |
| CH₃ | Xylene | A | 92–97 |

EXAMPLE 20

Preparation of 1-(hexahydrophthalimido)cyclohexanecarbonyl chlorides

Using the procedure described in Example 2 but substituting the acids listed in Table IX for 1-(3-chlorophthalimido)cyclohexanecarboxylic acid, the acid chlorides listed in Table II are prepared. These acid chlorides were characterized only by their infrared spectra and were then converted directly to the amides listed in Table X.

Table X

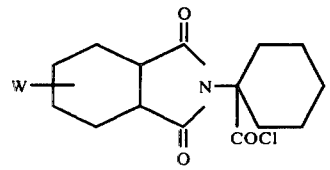

W = H or 4—CH₃

EXAMPLE 21

Preparation of 1-(hexahydrophthalimido)cyclohexanecarboxamides

Using the procedure described in Example 3 but substituting acid chloride listed in Table X for 1-(3-chlorophthalimido) cyclohexanecarbonyl chloride, the amides listed in Table XI are prepared.

Table XI

| W | Melting Point ° C | CL No. |
|---|---|---|
| H | 186–188 | 99,488 |
| 4-CH₃ | 150–152 | 99,622 |

EXAMPLE 22

Preparation of 3(or 6)-Chloro-N-(1-cyanocyclohexyl)-phthalomic acid

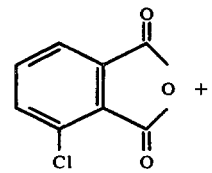

-continued

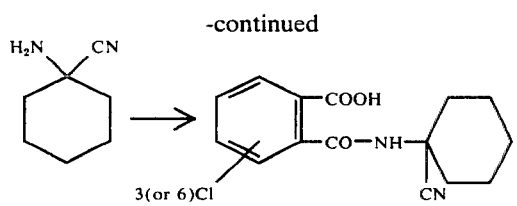

A mixture containing 18.26 g. 3chlorophthalic anhydride and 12.4 g. 1-aminocyclohexanecarbonitrile in 250 ml. ether is heated under reflux for 2 hours. The mixture was cooled and the crystalline solid product removed by filtration. The 3(or 6)-chloro-N-(1-cyanocyclohexyl)-phthalamic acid may be recrystallized from acetone/hexane to give analytically pure material m.p. 154°–155° C.

Similarly, when phthalic anhydride is substituted for 3-chlorophthalic anhydride, the product, N-(1-cyanocyclohexyl)-phthalamic acid, m.p. 154°–156° C. is formed.

EXAMPLE 23

Preparation of 3-Chloro-N-(1-cyanocyclohexyl)-phthalimide

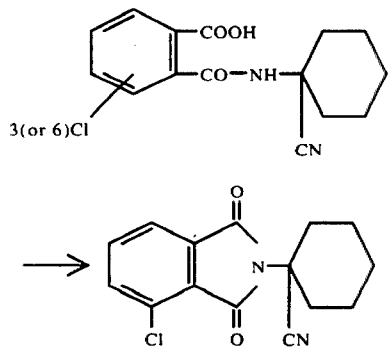

A slurry of 1.5 g. of 3(or 6)-chloro-N-(1-cyanocyclohexyl)-phthalamic acid in 10 ml. acetic; anhydride is heated at reflux for 4 hours. The anhydride is removed by evaporation at reduced pressure to leave a crystalline residue. The residue is recrystallized from isopropanol to give analytically prue 3-chloro-N-(1-cyanocyclohexyl)-phthalimide, m.p. 153°–154.5° C.

Similarly, when 3(or 6)-chloro-N-(1-cyanocyclohexyl)-phthalamic acid is replaced by N-(1-cyanocyclohexyl)pthalamic acid the product, N-(1-cyanocyclohexyl)-phthalimide, m.p. 115°–116.5° C. is formed.

EXAMPLE 24

Preparation of 1-(3-Chlorophthalimido)cyclohexanecarboxamide

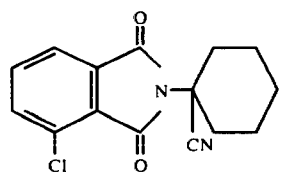

-continued

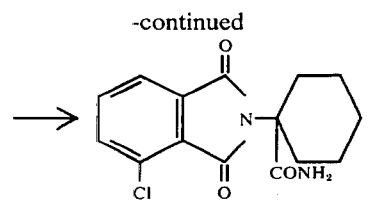

To a solution containing 300 mgs. 3-chloro-N-(1-cyanocyclohexyl)-phthalimide in 3 ml. methylene chloride is added, with good stirring, 0.38 ml. concentrated sulfuric acid. After 0.5 hour, ice is added and the aqueous phase extracted with chloroform. The organic phase is washed with water, dried and evaporated to give the 1-(3-chlorophthalimido)cyclohexanecarboxamide which can be purified by recrystallization from aqueous ethanol, m.p. 193°–194° C.

EXAMPLE 25

Preparation of 3-Trichloromethylphthalic Anhydride

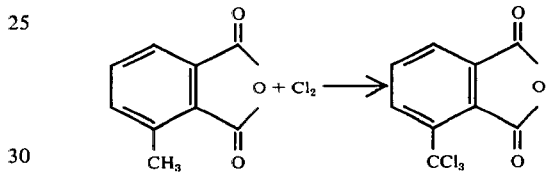

Into a stirred, molten mass of 45.85 g. of 3-metylphthalic anhydride at 145° C. is slowly passed chlorine gas while the reaction mixture is irradiated with a sum lamp. After 4 hours, the temperature is increased to 170° C. The temperature is further increased as follows: after 6½hours, 190° C., and after 14½ hours, 230° C., after a total of eighteen hours. The reaction mixture is allowed to cool to 100° C. Sixty ml of toluene is then added, and the solution is transferred to an erlenmeyer flask. It is then diluted with 60 ml of toluene plus 60 of hexane, followed by warming to affect solution, and cooling to precipitate the product. the resulting cystals are removed by filtration and washed with cold hexane leaving 65 g of a tan solid, m.p. 121°–124° C.

EXAMPLE 26

Preparation of 3-Trifluoromethylphthalic Anhydride

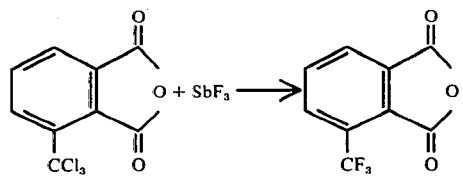

A mixture of 12.43 g of 3-trichloromethylphthalic anhydride, 12.5 g of antimony trifloride, and a few grams of sand are heated at 200° C. The molten mass is stirred for one hour. It is then cooled, stirred with benzene and water, and the mixture filtered and separated. The resulting organic solution is washed with water and brine, dried, and the solvent evaporated leaving 7.29 g. of a brown solid, m.p. 65°–67° C.

EXAMPLE 27

Preparation of 1-(3-trifluoromethylphthalimido)cyclohexanecarboxamide

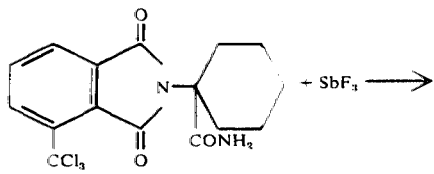

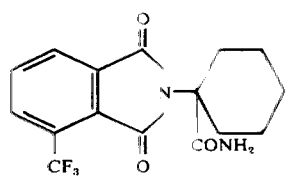

Equal weights of the trichloromethyl derivative and antimony trifluoride are heated together at 200° with some sand for 1 hour. The mixture is cooled, stirred with toluene and water, the mixture filtered and the organic phase separated. The organic phase is washed with water and brine, dried and the solvent evaporated to give the trifluoromethyl derivative which can be recrystallized fromm nitromethane, m.p. 166°–167° C.

Alternatively the same product can be obtained from the trifluoromethylphthalic anhydride using the methods described in Examples 1–3.

EXAMPLE 28

Preparation of 1-(3-dimethylaminophthalimido)cyclohexanecarboxamide

Reductive alkylation of 1-(3-nitrophthalimido) cyclohexanecarboxamide is carried out with formaldehyde and hydrogen in the presence of platinum metal catalyst at room temperature in ethanol to give the title compound, m.p. 166.5°–169° C.

EXAMPLE 29

Preparation of a mixture of 1-(3- and 4-chlorophthalimido)-cyclohexanecarboxamide

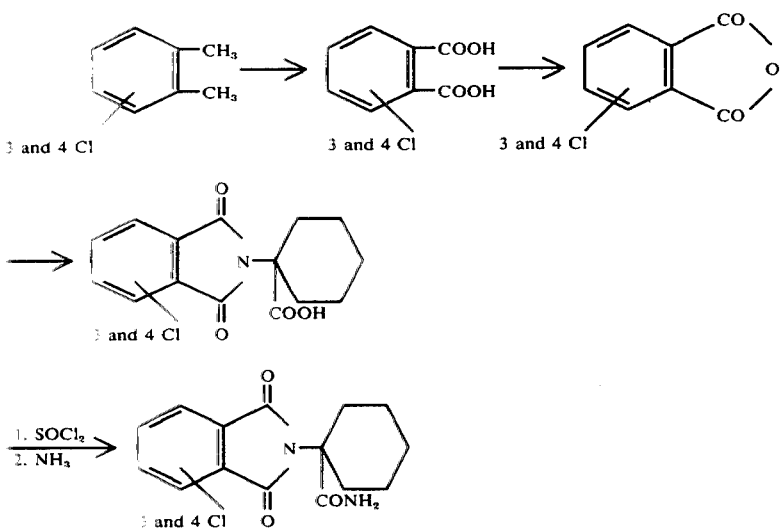

A mixture containing 14.0 g mixed chloroxylenes (approx. 55% 4-chloroxylene and 45% 3-chloroxylene) in 400 water containing 69 g potassium permanganate is heated under reflux for 4 hours. The mixture is filtered and the filtrate acidified with conc. $H_2SO_4$ to pH 1. Evaporation of the water leaves a solid residue which is extracted into a 1:1 mixture of chloroform: isopropanol. Evaporation of the solvent leaves the mixed 3- and 4-clorophthalic acids m.p, 115° C. (decomp).

The mixed chlorophthalic acids are heated in 50 ml acetic anhydride for one hour, the solvent is removed to give the mixed 3- and 4-chlorophthalic anhydrides m.p. 52°–66° C.

Condensation of the mixed anhydrides with 1-aminocyclohexanecarboxylic acid as described in Example 1 gives the mixed 1-(3- and 4-chlorophthalimido)cyclohexanecarboxylic acids m.p. 166°–177° C. which, when reacted with thionyl chloride in benzene as described in Example 2, gives the mixed 1(3- and 4-chlorophthalimido)cyclohexanecarbonyl chlorides as an oil. The reaction of the above-described carbonyl chlorides with ammonia as described in Example 3, gives the desired mixture named in the title, m.p. 167°–175° C.

EXAMPLE 30

Preparation of 1-(3-bromophthalimido)cyclohexanecarboxamide,

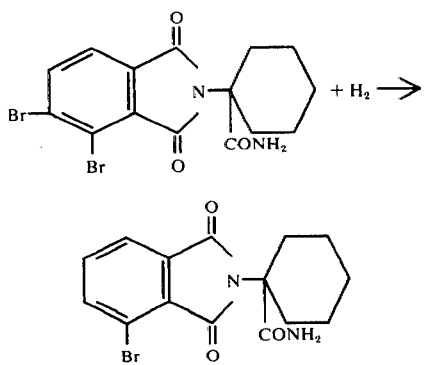

A solution of 1-(3,4-dibromophthalimido)cyclohexanecarboxamide in acetic acid containing one equivalent of sodium acetate is reduced with hydrogen in the presence of palladium on carbon to give the product 1-(3-bromophthalimido) cyclohexanecarboxamide, m.p. 199°–200° C.

EXAMPLE 31

Preparation of 3-benzyloxy-6-methylphthalic anhydride

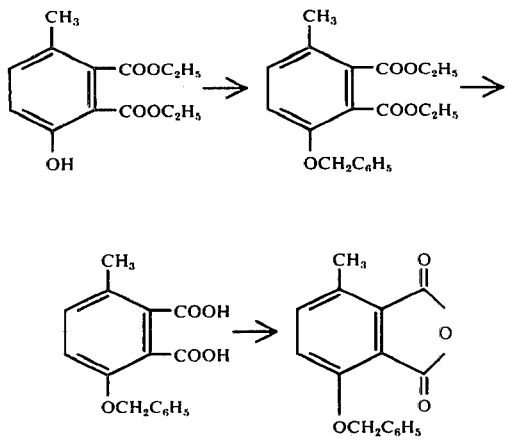

To a stirred solution containing 25.2 g phenol in 250 ml dry t-butanol was added 11.2 g potassium t-butoxide in a nitrogen atmosphere. After 15 minutes, 17.1 g benzyl bromide is added dropwise. The reaction is stirred overnight and then poured into water and the product extracted into ether. The extract is washed successively with water, cold 2N NaOH, water and brine, dried and the solvent evaporated to leave 32.9 g of crude diethyl 3-benzyloxy-6-methylphthalate.

The crude ester is heated under reflux for 3 hours in 150 ml water and 100 ml 95% ethanol containing 20 g NaOH. The mixture is poured into water and the resulting solid removed by filtration, washed with water and air-dried to give 24.4 g crude 3-benzyloxy-6-methylphthalic acid.

The crude phthalic acid prepared above is heated in 150 ml acetic anhydride for two hours. The solvent is removed under reduced pressure and the crystalline residue collected and washed with ether. The anhydride may be recrystallized from nitromethane to give an analytical sample m.p. 200°–203° C.

EXAMPLE 32

Preparation of 1-[3-(ethylsulfonyl)-6-methylphthalimido]-cyclohexanecarboxylic acid.

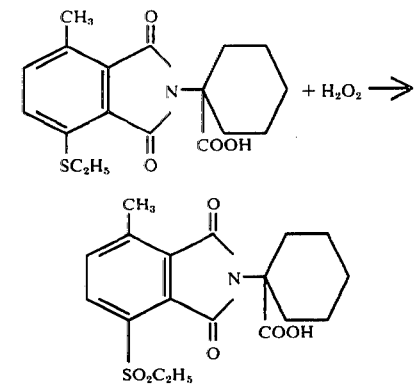

To a solution of 15.6 g 30% hydrogen peroxide in 15 ml acetic acid is added 8.9 g of the sulfide in 80 ml acetic acid and the mixture heated under reflux for 1.5 hours. The volume of the solution is reduced by three quarters and the residue is poured into water. The product is extracted into ether, the extract washed with water, the organic phase dried and the solvent evaporated. The residue is crystallized from benzene to give the ethylsulfonyl derivative with m. p. 152°–153° C.

EXAMPLE 33

Preparation of 1-(3-hydroxy-6-methylphthalimido)-cyclohexanecarboxamide

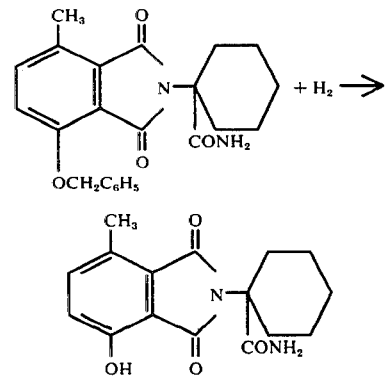

A solution containing 2.7 g of the benzyl ether in 100 ml acetic acid is shaken in an atmosphere of hydrogen in the presence of 2 g 5% palladium on carbon. The hydrogenation is complete in 20 minutes and the catalyst is removed by filtration and the filtrate evaporated to give 500 mg product. The filter cake is washed with dimethylformamide and the filtrate poured into water. The precipitate is removed by filtration, washed with water and air-dried to give a further 800 mg product. Recrystallization of the combined fractions from acetic acid gave analytically pure product, m.p. 265° C. (decomp).

EXAMPLE 34

Plant Growth Regulating Effects of Phthalimido Derivatives on a Variety of Plant Species In these tests, a 50/50 water/acetone mixture containing 1-(3-chlorophthalimido)cyclohexanecarboxamide is sprayed on the soil surface of 2 square foot flats in sufficient amount to provide 4 pounds per acre of active compound. Seeds of a variety of plants are then placed on the treated soil and covered with untreated soil to a depth of 1 inch. The planted flats are then placed on greenhouse benches, watered and maintained in accordance with normal greenhouse practices. All tests are run in duplicate and untreated flats are used as controls.

All flats are examined periodically and the results observed and recorded. The plant species used are indicated below in Table XII along with emergence times and plant height for each species. All tests are terminated 28 days after planting.

TABLE XII

| Plant Species Employed | | | |
|---|---|---|---|
| Cotton | Corn (Sweet) | Sugar beet | Celery |
| Pea | Wheat | Soybean | Sudangrass |
| Sorghum | Tomato | Alfalfa | Peanut |
| Rape | Navy Bean | Rice | Safflower |
| Oat | Lima Bean | Radish | Cabbage |
| Cucumber | Potato | Birdsfoot trefoil | Snap bean |
| Flax | Barley | Carrot | Lettuce |

| Emerged in | Emergence Times Treated Plants |
|---|---|
| 3 days | Radish and Alfalfa |
| 4 days | Barley and Soybean, Cucumber, Sugar Beet, Sudangrass, Wheat, Rape, Pea |
| 5 days | Flax, Corn, Safflower, Oat, Navy bean, Cotton, Lima bean, Cabbage, Snap bean, Birdsfoot trefoil |
| 6 days | Sorghum, Tomato, Potato |
| 7 days | Peanut, Lettuce, Rice, Carrot |
| 12 days | Celery |

| Emerged in | Control Plants |
|---|---|
| 6 days | Cotton, Soybean |
| 7 days | Navy bean, Snap bean |
| 8 days | Tomato |
| 10 days | Potato |
| 15 days | Celery |

Remaining plants emerged at the same time as treated plants.

Observed Plant Height 28 Days After Treatment

| Plants 50% or More Taller than Controls | | | |
|---|---|---|---|
| Potato | Soybean | Oats | Sugar beet |
| Lettuce | Cucumber | Rice | Cotton |
| Lima bean | Wheat | Corn | Flax |
| Snap bean | Barley | Tomato | Rape |

| Plants 25% to 50% Taller than Controls | | |
|---|---|---|
| Radish | Sudangrass | Sorghum |
| Carrot | Cabbage | Navy bean |
| Safflower | Pea | Peanuts |

| Plants Approximately the Same Height as Controls |
|---|
| Alfalfa |
| Birdsfoot trefoil |
| Celery |

EXAMPLE 35

Plant Growth Regulating Effect of Phthalimido Derivatives on Xanthia Tobacco In this test, untopped plants of approximate similar height are treated with 50/50 acetone/water mixtures containing 100 ppm., 200 ppm., or 400 ppm. of 1-(3-chlorophthalimido(cyclohexanecarboxamide and then placed on greenhouse benches. All treatments are replicated four times and untreated plants are used as controls. Twenty-eight days after treatment, all plants examined and measured.

Data obtained are reported below in Table XIII, where it can be seen that plants treated with 100 ppm. of test compound have an 18% gain over controls and those treated with 200 ppm. and 400 ppm. show 28% and 50% gains, respectively, over controls.

Five weeks after treatment, the tallest and shortest plants from each treatment are cut and weighed and the average weight per treatment determined. From the data, it can be seen that the percent gain of treated plants over untreated controls is from 30% to 70%.

The dry weights of the two middle plants in the four replicates is taken nine weeks after treatment and shows a 12% to 54% increase over untreated controls. These data are given below in Table XIII.

TABLE XIII

| | Xanthin Tobacco Height in Inches at Rates of: | | | Control Acetone/Water 50/50 |
|---|---|---|---|---|
| Compound | 400 ppm. (16 mg./Plant) | 200 ppm. (8 mg./Plant) | 100 ppm. (4 mg./Plant) | |
| 1-(3-Chlorophthal-imido)cyclohexane-carboxamide | | | | |
| Replicate I | 35 | 28 | 24.5 | 23 |
| II | 33 | 28 | 27 | 23 |
| III | 33 | 30 | 29 | 26 |
| IV | 37 | 32 | 28.5 | 20 |
| Average | 34.5 | 29.5 | 27.2 | 23 |

| | % Gain Over Controls at Rates of: | | |
|---|---|---|---|
| Compound | 400 ppm. | 200 ppm. | 100 ppm. |
| 1-(3-Chlorophthal- | | | |

TABLE XIII-continued

Xanthin Tobacco

| | | | |
|---|---|---|---|
| imido)cyclohexane-carboxamide | +50% | +20% | +18% |

| | Wet Weights in Grams of Two Replicates (The Tallest and the Smallest) at Treatment Rates of: | | | Control Acetone/Water 50/50 |
|---|---|---|---|---|
| Compound | 400 ppm. | 200 ppm. | 100 ppm. | |
| 1-(3-Chlorophthal-imido)cyclohexane-carboxamide | | | | |
| Replicate I | 111 | 84 | 100 | 75 |
| II | 151 | 114 | 115 | 77 |
| Average | 131 | 99 | 107.5 | 76 |

| | % Gain Over Controls in Wet Weight at Rates of: | | |
|---|---|---|---|
| Compound | 400 ppm. | 200 ppm. | 100 ppm. |
| 1-(3-Chlorophthal-imido)cyclohexane-carboxamide | +72% | +30% | +41% |

Treated plants were taller than untreated plants, but they did not have more leaves. The internodal spaces were elongated, yet the stems did not appear to be thinner than the checks.

| | Dried Weights in Grams of Two Replicates (Two Middle Plants) at Treatment Rates of | | | Control Acetone/Water 50/50 |
|---|---|---|---|---|
| Compound | 400 ppm. | 200 ppm. | 100 ppm. | |
| 1-(3-Chlorophthal-imido)cyclohexane-carboxamide | 31.5 | 23 | 26.5 | 20.5 |

| | % Gain Over Controls in Dry Weight at Rates of: | | |
|---|---|---|---|
| Compound | 400 ppm. | 200 ppm. | 100 ppm. |
| 1-(3-Chlorophthal-imido)cyclohexane-carboxamide | +53.6% | +12.2% | +29% |

EXAMPLE 36

Seed Treatment to Improve Fresh Weights and Dry Weights of Plants.

In these test, seeds of field corn (DeKalb XL-45) are soaked for 2 hours in water or an aqueous solution containing 10 ppm., 100 ppm. or 1000 ppm. of 1-(3-chlorophthalimido)cyclohexanecarboxamide. After such treatment, the seeds are planted, five per pot, in 5-inch plastic pots and placed in the greenhouse where they are cared for in accordance with standard greenhouse procedures.

Three weeks after treatment, all plants are measured, harvested and weighed. After weighing, the harvested plants are dried and dry weights from each treatment determined. Data obtained are given below in Table XIV, where it can be seen that about a 20 to 36% increase in height 15 to 28% increase in fresh weight, and a 5 to 21% increase in dry weight of treated plants is obtained.

TABLE XIV

Seed Treatment to Improve Fresh Weight, Height and Dry Weight of Field Corn

Test Compound - 1-(3-CHlorophthalimide)cyclohexanecarboxamide

| Treatment Rates | Fresh Weights of Tops in Grams | | | Dry Weights of Tops in Grams | | | % Change | |
|---|---|---|---|---|---|---|---|---|
| | Replicate I | Replicate II | Replicate III | Replicate I | Replicate II | Replicate III | Fresh Wt. Average 3 Replicates | Dry Wt. Average 3 Replicates |
| 0 ppm. | 14.8 | 19.5 | 20.1 | 1.70 | 2.03 | 1.90 | — | — |
| 10 ppm. | 20.9 | 21.3 | 20.8 | 2.00 | 2.02 | 1.94 | +15 | +5 |
| 100 ppm. | 22.0 | 24.5 | 21.9 | 2.18 | 2.21 | 2.18 | +26 | +16 |
| 1000 ppm. | 23.2 | 25.3 | 21.5 | 2.24 | 2.26 | 2.33 | +28 | +21 |

| Treatment Rates | Height (cm.) to Second Leaf | | | Total Height (cm.) | | | % Change | |
|---|---|---|---|---|---|---|---|---|
| | Replicate I | Replicate II | Replicate III | Replicate I | Replicate II | Replicate III | Second Leaf Average | Total Average |
| 0 ppm. | 9 | 9 | 9 | 30 | 37 | 32 | — | — |
| 10 ppm. | 10 | 12 | 10 | 38 | 41 | 37 | +19 | +18 |
| 100 ppm. | 10 | 13 | 11 | 39 | 42 | 40 | +25 | +21 |

TABLE XIV-continued

Seed Treatment to Improve Fresh Weight, Height and Dry Weight of Field Corn

Test Compound - 1-(3-CHlorophthalimide)cyclohexanecarboxamide

| 1000 ppm. | 12 | 13 | 12 | 43 | 45 | 42 | +36 | +30 |
|---|---|---|---|---|---|---|---|---|

EXAMPLE 37

Plant Growth Regulating Effects of Phthalimido Derivatives

In these tests, seeds and seed pieces of tomato and potato, respectively, are placed in rows on a soil surface in flats. A spray, 50/50 acetone/water containing the test compound, is applied over the seed and soil surface in sufficient amount to provide 0.5, 1, 2 or 4 pounds per acre of test conpound. The seed is covered with about ½ inch of untreated soil and watered. The flats are placed on greenhouse benches and cared for in accordance with greenhouse practices. These weeks after treatment, the flats are examined and the height and fresh weight of the tomato and potato plants determined. The number of stems on the potato plants are also counted since the number of stem per plant is an indication of the number of potatoes that will be set. Data obtained are reported below in Table XV.

TABLE XV

Plant Growth Regulating Effects of Test Compounds

| | | Tomato | | | Potato | |
|---|---|---|---|---|---|---|
| Compounds | Rate lbs./acre | Height cm. | Grams 5 Plants French Weight | Height cm. | Number of Stems | Fresh Weight Grams |
| 2-(1-(3-chlorophthalimido)-cyclohexylcarbonyl]-1,1,1-trimethylhydrazinium chloride | ½ | 11 | 8 | 20 | 24 | 109 |
| | 1 | 12 | 9 | 21 | 23 | 124 |
| | 2 | 11 | 9.5 | 21 | 21 | 130 |
| | 4 | 11 | 10.5 | 25 | 21 | 181 |
| 1-(3-chlorophthalimido)-cyclohexanecarboxamide | ½ | 17 | 17 | 32 | 16 | 134 |
| | 1 | — | — | 33 | 13 | 109 |
| | 2 | 17 | 15.5 | 34 | 25 | 147.5 |
| | 4 | 16 | 10.5 | 36 | 19 | 104 |
| α-(3-chlorophthalimido)-α-methyl-α-iso propylacetamide | ½ | 11 | 10 | 23 | 19 | 145 |
| | 1 | 10 | 9.5 | 21 | 9 | 85.5 |
| | 2 | 7 | 3 | 19 | 7 | 30 |
| | 4 | 6 | 1.5 | 13 | 2 | 22 |
| 1-(3-chlorophthalimido)-cycloheptanecarboxamide | ½ | 8 | 7 | 22 | 19 | 155 |
| | 1 | 8 | 8.5 | 18 | 13 | 65.5 |
| | 2 | 11 | 14.5 | 20 | 21 | 122 |
| | 4 | 6 | 4 | 22 | 22 | 145 |
| 1-(3-chlorophthalimido)-2,2-dimethylhydrazide cyclohexanecarboxylic acid | ½ | 11 | 12.5 | 19 | 18 | 103 |
| | 1 | 12 | 13 | 19 | 15 | 137 |
| | 2 | 12 | 14.5 | 21 | 19 | 179 |
| | 4 | 12 | 14.5 | 24 | 12 | 123.5 |
| 1-(3-chlorophthalimido)-cyclopentanecarboxylic acid | ½ | 12 | 16.5 | 18 | 14 | 113.5 |
| | 1 | 11 | 14 | 18 | 19 | 95.5 |
| | 2 | 12 | 12 | 20 | 26 | 149.5 |
| | 4 | 10 | 12 | 18 | 20 | 139.0 |
| α-(3-chlorophthalimido)-α- | ½ | 15 | 14.5 | 17 | 16 | 84.5 |
| | 1.5 | 17.5 | 24 | 19 | 188 | |
| | 2 | 15 | 13.0 | 24 | 16 | 98.5 |
| | 4 | 13 | 11.0 | 26 | 20 | 177 |
| 1-(3-nitrophthalimido)-cyclohexanecarboxylic acid | ½ | 12 | 12.5 | 25 | 17 | 146.5 |
| | 1 | 13 | 10.0 | 22 | 18 | 182.5 |
| | 2 | 13 | 12.5 | 27 | 13 | 170.5 |
| | 4 | 15 | 13.0 | 21 | 11 | 150.5 |
| α-(3-nitrophthalimido)-α-isobutyl-α-methylacetamide | ½ | 14 | 15.0 | 23 | 26 | 182 |
| | 1 | 10 | 11.5 | 20 | 21 | 141 |
| | 2 | 11 | 11.5 | 21 | 16 | 117 |
| | 4 | 9 | 7.5 | 23 | 19 | 174 |
| 1-(3-chlorophthalimido)-cyclohexamecarboxylic acid ethyl ester | ½ | 10 | 11.5 | 22 | 20 | 152 |
| | 1 | 7 | 7.0 | 21 | 17 | 144 |
| | 2 | 12 | 10.0 | 23 | 15 | 143 |
| | 4 | 10 | 8.5 | 23 | 13 | 98 |
| N,N-dimethyl-1-(3-nitro-phthalimido)cyclohexane-carboxamide | ½ | 8 | 6 | 19 | 19 | 135.5 |
| | 1 | 9 | 9.5 | 23 | 18 | 192 |
| | 2 | 12 | 11.0 | 23 | 13 | 141 |
| | 4 | 11 | 9.5 | 21 | 28 | 160.5 |
| 1-(3-chlorophthalimido)-N,N-dimethyl cyclohexane-carboxamide | ½ | 13 | 12.0 | 22 | 19 | 138 |
| | 1 | 12 | 12.5 | 18 | 19 | 119 |
| | 2 | 10 | 8.5 | 21 | 17 | 159 |
| | 4 | 10 | 12.5 | 21 | 15 | 145 |
| 1-(3-nitrophthalimido)-cyclohexanecarboxamide | ½ | 13 | 13.0 | 20 | 18 | 169 |
| | 1 | 11 | 13.5 | 18 | 14 | 111.5 |
| | 2 | 12 | 13.0 | 20 | 22 | 152 |

TABLE XV-continued

Plant Growth Regulating Effects of Test Compounds

| Compounds | Rate lbs./acre | Tomato Height cm. | Grams 5 Plants French Weight | Potato Height cm. | Number of Stems | Fresh Weight Grams |
|---|---|---|---|---|---|---|
| | 4 | 10 | 10.0 | 19 | 21 | 132.5 |
| 1-(3-chlorophthalimido)-cyclophtanecarboxamide | ½ | 14 | 14.5 | 26 | 27 | 212 |
| | 1 | 11 | 9.5 | 23 | 17 | 124.5 |
| | 2 | 12 | 12.0 | 30 | 23 | 204 |
| | 4 | 12 | 11.5 | 32 | 15 | 140 |
| 1-(3-chlorophthalimido)-cycloheptanecarboxylic acid | ½ | 10 | 7.5 | 19 | 18 | 142.5 |
| | 1 | 10 | 7.0 | 24 | 15 | 197 |
| | 2 | 11 | 10.0 | 20 | 17 | 121.5 |
| | 4 | 10 | 13.5 | 25 | 18 | 184 |
| 1-phthalimidocyclohexane-carboxylic acid | ½ | 13 | 18.0 | 11 | 14 | 62 |
| | 1 | 12 | 9.5 | 22 | 13 | 111 |
| | 2 | 12 | 14.0 | 24 | 13 | 111 |
| | 4 | 11 | 10.5 | 23 | 16 | 142.5 |
| 1-phthalimidocyclohexane-carboxamide | ½ | 7 | 6.0 | 22 | 14 | 80.5 |
| | 1 | 6 | 5.0 | 24 | 16 | 148.5 |
| | 2 | 10 | 9.0 | 20 | 17 | 75.5 |
| | 4 | 10 | 7.0 | 26 | 17 | 76.5 |
| 1-phthalimidocyclopentane-carboxamide | ½ | 10 | 11 | 13 | 14 | 33.5 |
| | 1 | 8 | 7.5 | 19 | 17 | 118.5 |
| | 2 | 11 | 11.5 | 27 | 22 | 121.5 |
| | 4 | 10 | 10.0 | 28 | 14 | 135.5 |
| Controls Average of 6 Replications 3 Water & 3 Acetone/Water | — | 10.6 | 19.5 | 17.3 | | 122.6 |

EXAMPLE 38

Effect of 1-(3-Chlorophthalimido)cyclohexanecarboxamide on Potatoes

In these tests, potato seed pieces are placed on the surface of soil in deep flats approximately 2 feet square and sprayed with an aqueous solution of test compound in a 50/50 acetone/water mixture. Applications are sufficient to provide from 0 to 4 pounds per acre of active compound, and after spraying the seed pieces are covered with soil. The flats are placed in the greenhouse and cared for in accordance with normal greenhouse procedure. Eight weeks after treatment, the plants with roots and tubers are harvested and examined. From the data obtained, which is reported below in Table XVI, it can be seen that the shoots of treated plants are taller, stronger and weigh more than untreated controls. The number of shoots increases 16% to 33%, the roots are heavier, and the number of tubers initiated are higher.

TABLE XVI

Potato Yield

Compounds Used in These Tests
1-(3-Chlorophthalimido)cyclohexanecarboxamide

| Treatment ppm. | Shoots Number | Height cm. | Weight gram | Tubers Number | Roots Weight gram |
|---|---|---|---|---|---|
| Control | 6 | 41 | 126.2 | 9 | 77.2 |
| 10 | 6 | 49 | 147.8 | 9 | 100.5 |
| 100 | 7 | 48 | 123.0 | 10 | 91.1 |
| 1,000 | 7 | 64 | 134.6 | 9 | 101.0 |
| 10,000 | 8 | 96 | 138.4 | 19 | 118.7 |
| Control | 5 | 51 | 111.2 | 8 | 82.7 |
| 10 | 7 | 52 | 144.2 | 11 | 123.5 |
| 100 | 6 | 56 | 119.0 | 9 | 83.7 |
| 1,000 | 8 | 73 | 155.4 | 15 | 108.8 |
| 10,000 | 8 | 100 | 181.8 | 22 | 106.7 |

EXAMPLE 39

Improved Stem Strength in Xanthia Tobacco and Effect on Plant Height and Leaf Number In the following tests, Xanthia tobacco plants approximately two months old and growing in individual pots are treated at first flowering with an aqueous/acetone (50/50) mixture containing 100 ppm. to 1600 ppm. or 800 ppm. to 3200 ppm. of 1(3-chlorophthalimide)cyclohexanecarboxamide. One month after treatment, the plants are examined and the stems harvested to determine the dry weights thereof or the number of leaves counted and the plants measured. Data obtained are provided below in Table XVII.

TABLE XVII

Xanthia Tobacco

| Compound | Dried Weights of Tobacco Atoms in Grams (4 Replicates) | | | | | Control |
|---|---|---|---|---|---|---|
| | 1600 ppm. | 800 ppm. | 400 ppm. | 200 ppm. | 100 ppm | 0 |
| 1-(3-chlorophthal- | | | | | | |

TABLE XVII-continued

Xanthia Tobacco

| imido)cyclohexane-carboxamide | 74 | 86 | 87 | 83 | 83 | 72.6 |
|---|---|---|---|---|---|---|
| % Gain | 1.9% | 18.4% | 19.8% | 14% | 14% | m |

|  | 3200 ppm. | | 1600 ppm. | | 800 ppm. | | Control 0 | |
|---|---|---|---|---|---|---|---|---|
| Compound | Height Inches | Number Leaves | Height Inches | Number Leaves | Height Inches | Number Leaves | Height Inches | Number Leaves |
| 1-(3-chlorophthal-imido)cyclohexane-carboxamide | 75 | 47 | 78 | 50 | 54.5 | 45 | 38*<br>42** | 43*<br>48** |

*Replicate I
**Replicate II

EXAMPLE 40

Effect of Phthalimide Derivative on Potato Plants

In these tests, 50/50 aqueous/acetone mixtures containing from 0 to 10,000 ppm. of 1-(3-chlorophthalimido)-cyclohexanecarboxamide are prepared. Seed pieces of potato (Superior variety) are dipped for 1 or 5 minutes in the selected solution and then planted in flats and placed in the greenhouse. The plants are cared for in accordance with normal greenhouse procedures, and 2 months after treatment and the plants are examined. The number of shoots and tubers developed are counted, the height and weight of the shoots and the root weight is also determined. These data are reported below in Table XVIII, where it can be seen that there is a 22% to 60% increase in shoot number, a 2% to 134% increase in shoot height, up to 63% increase in shoot weight, up to 170% increase in tuber number, and as much as 53% increase in root weight.

TABLE XVIII

Effect of 1-(3-Chlorophthalimido)cyclohexanecarboxamide on Dipped Potato Tubers (Superior Variety)

|  | Shoot Number | | | | | Shoot Height (gm.) | | | | | Shoot Weight (grams) | | | | |
|---|---|---|---|---|---|---|---|---|---|---|---|---|---|---|---|
|  | Replicate | | | | Plus or Minus % | Replicate | | | | Plus or Minus % | Replicate | | | | Plus or Minus % |
| Treatment | I | II | III | Average |  | I | II | III | Average |  | I | II | III | Average |  |
| *A-1 | 7 | 5 | 6 | 6 | — | 33 | 42 | 48 | 41 | — | 116.8 | 126.2 | 135.6 | 126.2 | — |
| A-2 | 7 | 5 | 10 | 7.3 | +22% | 50 | 50 | 48 | 49 | +19% | 153 | 136.7 | 153.5 | 147.7 | +16% |
| A-3 | 6 | 7 | 9 | 7.3 | +22% | 50 | 48 | 46 | 48 | +17% | 130 | 109.7 | 128.2 | 122.6 | −4% |
| A-4 | 9 | 6 | 7 | 7.3 | +22% | 60 | 68 | 65 | 64 | +56% | 134.5 | 139.8 | 129.3 | 134.5 | +4% |
| A-5 | 8 | 9 | 7 | 8 | +33% | 90 | 90 | 110 | 96 | +34% | 165.4 | 161.3 | 88.0 | 138.2 | +9% |
| B-1 | 6 | 4 | 5 | 5 | — | 46 | 56 | 50 | 50 | — | 111.2 | 105.5 | 116.8 | 111.1 | — |
| B-2 | 8 | 8 | 6 | 7.3 | +46% | 50 | 50 | 55 | 51 | +2% | 154 | 130 | 148.6 | 144.2 | +29% |
| B-3 | 7 | 9 | 6 | 7.3 | +46% | 53 | 55 | 58 | 55 | +10% | 118.7 | 106.8 | 141.4 | 122.3 | +9% |
| B-4 | 10 | 9 | 6 | 8.3 | +66% | 73 | 83 | 65 | 73 | +46% | 147.1 | 174.1 | 145 | 155.4 | +30% |
| B-5 | 7 | 9 | 8 | 8 | +60% | 94 | 100 | 105 | 99 | +98% | 177.3 | 181.5 | 186.5 | 181.7 | +63% |

|  | Tuber Number | | | | | Root Weight (grams) | | | | |
|---|---|---|---|---|---|---|---|---|---|---|
|  | Replicate | | | | Plus or Minus % | Replicate | | | | Plus or Minus % |
| Treatment | I | II | III | Average |  | I | II | III | Average |  |
| *A-1 | 10 | 10 | 8 | 9.3 | — | 69.5 | 75.3 | 86.7 | 77.1 | — |
| A-2 | 5 | 13 | 9 | 9 | −4% | 132.6 | 82.3 | 86.3 | 100.5 | +30% |
| A-3 | 14 | 9 | 8 | 10.3 | +7% | 115.3 | 81.3 | 76.6 | 91.0 | +18% |
| A-4 | 7 | 7 | 15 | 9.6 | +3% | 111.2 | 103.4 | 88.4 | 101.0 | +31% |
| A-5 | 11 | 27 | 20 | 19.3 | +107% | 104.7 | 129 | 122.4 | 118.7 | +53% |
| B-1 | 9 | 9 | 6 | 8 | — | — | 78.7 | 86.4 | 82.5 | — |
| B-2 | 11 | 9 | 12 | 10.6 | +32% | 101.4 | 195.7 | 83.3 | 126.8 | +53% |
| B-3 | 10 | 6 | 10 | 8.6 | +7% | 86.5 | 67.8 | 96.8 | 83.7 | +1% |
| B-4 | 16 | 19 | 10 | 15 | +87% | 104.8 | 122 | 99.6 | 108.8 | +31% |
| B-5 | 15 | 32 | 18 | 21.6 | +170% | 86.1 | 94.1 | 140 | 106.7 | +29% |

*Concentration:  1 = 0 ppm.
                2 = 10 ppm.
                3 = 100 ppm.
                4 = 1,000 ppm.
                5 = 10,000 ppm.

Duration of Dip A = 1 minute
Duration of Dip B = 5 minutes

EXAMPLE 41

Effect of Phthalimide Derivatives on Woody Plants

In these tests, resting Euonymous (woody) plants growing in individual pots are treated with 50/50 aqueousacetone solutions containing sufficient amounts of the test phthalimide to provide 0, 5 or 15 pounds per acre thereof. The phthalimides used are 4-chloro-$\alpha$-isobutyl-$\alpha$-methyl-1,3-dioxo-2-isoindoleacetamide and 1-(3-chlorophthalimido)-cyclohexanecarboxamide, and application is made as a soil drench. The plants are measured and the number of branches counted at treatment. Two months after treatment, the plants are again measured and the number of branches counted. Data obtained are reported below in Table XIX where it can be seen that there is a 10% to 55% increase in leader growth and a 23% to 54% increase in the number of branches on treated plants.

seeds have been mixed in an amount sufficient to provide each pot with approximately 625 Fescue seeds.

To prepare the test compounds, 20 mg. of the com-

TABLE XIX

Effect of 4-Chloro-α-isobutyl-α-methyl-1,3-dioxo-2-isoindolinoacetamide and 1-(3-Chlorophthalimido)cyclohexanecarboxamide on Euonymous Soil Drench Treatment

| Compound | Rate lbs./acre | Height of Leader in cm. at Treatment Replicate | | | | Number Branches at Treatment Replicate | | | | Leader - Added Growth in cm. Replicate | | | | Number Branches Replicate | | | | Average % Leader Growth Four Replicates | Average % Increase in Number of Branches |
|---|---|---|---|---|---|---|---|---|---|---|---|---|---|---|---|---|---|---|---|
| | | I | II | III | IV | I | II | III | IV | I | II | III | IV | I | II | III | IV | | |
| 1-(3-chlorophthal-imido)cyclohex- | 15 | 24 | 21.5 | 37 | 41 | 6 | 9 | 2 | 2 | 17 | 21 | 8 | 23 | 9 | 9 | 4 | 4 | +55% | +36% |
| ane-carboxamide | 5 | 21.5 | 25.5 | 32 | 38 | 3 | 6 | 6 | 2 | 9 | 9 | 12 | 7 | 4 | 7 | 7 | 3 | +31% | +23% |
| 4-chloro-α-isobutyl-α-methyl-1,3-dioxo-2-isoindoline- | 15 | 19.5 | 21.5 | 43.5 | 28 | 6 | 5 | 5 | 7 | 2 | 4 | 2 | 4 | 8 | 6 | 10 | 8 | +10% | +40% |
| acetamide | 5 | 21.5 | 24 | 31 | 38 | 4 | 10 | 3 | 3 | 4 | 8 | 2 | 7 | 5 | 11 | 9 | 6 | +18% | +54% |
| Control | 0 | 39.5 | 39.5 | 23.5 | 23 | 4 | 6 | 6 | 6 | 0 | 0 | 0 | 0 | 4 | 6 | 6 | 6 | 0% | 0% |
| Control | 0 | 28 | 21.5 | 16.5 | 24 | 7 | 14 | 2 | 4 | 0 | 0 | 0 | 0 | 7 | 14 | 2 | 4 | 0% | 0% |

EXAMPLE 42

Effect of Phthalimido Derivatives on Pod Setting of Soy-beans

In these tests, soybeans (cv Corsoy) are planted in individual pots and treated with 50/50 aqueous/acetone mixtures containing from 0 to 2 pounds per acre of the active phthalimide, 1-(3-chlorophthalimido)cyclohexanecarboxamide. The pots are then placed in the greenhouse and cared for in usual fashion. Two months after treatment, the plants are examined and the height of attachment of the first pod above the ground determined for each plant. From the data obtained, it can be seen in Table XX that the height of attachment of the first pod of treated plants is from 10 to 22 centimeters above those of untreated plants.

TABLE XX

| Compound | Rate lbs./acre | cm. Above Ground of Attachment of First Pod |
|---|---|---|
| 0 | — | 12 cm. |
| 1-(3-chlorophthal-imido)cycylohex-anecarboxamide | 1 | 20 cm. |
| | 2 | 32 cm. |

EXAMPLE 43

Evaluation of Phthalimides for Plant Growth Regulant Activity

In these tests, containers are filled to within ½ inch of the top with greenhouse potting soil, tamped, and three Amsoy soybeans are placed in each pot. The pot is filled to the top with soil in which Kentucky 31 Fescue pound is placed into a two-ounce, wide-mouth glass bottle and dissolved or dispersed in a 50/50 acetone/water mixture sufficient to prepare a 1,000 ppm. solution or suspension.

An addition of 5 ml. of the 1,000 ppm. solution in each cup is equivalent to 10 lbs./acre.

Just prior to the application of the compounds, the test pots are lightly watered to prevent formation of air pockets and channelling routes during aplication which would prevent even distribution of the test compound in the soil. Application is accomplished by dispensing 5 ml. of solution or suspension evenly over the surface of the soil with a pipettor. Three replications are used for each compound.

The test is conducted weekly. Each test includes 5 ml. of 1:1 acetone:water controls, 5 ml. water controls as a standard for comparison of activity from test to test. The treated plants are benched in the greenhouse and normal watering practices are followed. Minimum day and night temperatures of 65° F. are maintained during cooler portions of the year. Normal daily temperature fluctuations occur during the summer season. Data obtained are reported below in Table XXI.

Data Recording

Initial observations are made at three to five days after treatment for early germination of both test species. Physiological or morphological changes from the norm are noted during the test period. Final observations are made at 2 to 3 weeks after treatment (dependent on time of year). At this time, measurements of the height of plants of both species are made. From these measurements percent increases or decreases as compared to control plants are calculated.

TABLE XXI

| | 10 lbs/Acre Preemergence | | | |
|---|---|---|---|---|
| | % Increase or Decrease in Height Compared to Control | | | |
| | Soybeans | | Fescue | |
| Compound | First Measurement | Final Measurement | First Measurement | Final Measurement |
| 1-Phthalimidocyclo-hexanecarboxamide | — | 58 E.G.* | — | 46 E. G. |
| α-(3-chlorophthal-imido)-α-isopropyl-α-methylacetamide | 28 | 36 Phy. | 38 | 36 Phy. |
| α-(3-chlorophthal-imido)-α-isobutyl- | | | | |

TABLE XXI-continued

| | 10 lbs/Acre Preemergence | | | |
|---|---|---|---|---|
| | % Increase or Decrease in Height Compared to Control | | | |
| | Soybeans | | Fescue | |
| Compound | First Measurement | Final Measurement | First Measurement | Final Measurement |
| α-methylacelamide | N | N | 21 | 15 |
| Cyclohexanecarboxamide, 1-(3-chlorophthalimido)- | 73 (7-10) | 73 (7-21) | 51 | 49 |
| Cyclopentanecarboxamide, 1-(3-chlorophthalimido) | N | out | 24 | 10 |
| Cyclohexanecarboxylic acid, 1-phthalimido- | -13 | out | -33 | -31 |
| Cyclopentanecarboxamide, 1-phthalimido- | — | 23 E.G. | — | 17 E.G. |
| Cycloheptanecarboxamide, 1-(3-chlorophthalimido)- | — | N D.G. | — | 41 D.G. |
| Cyclohexanecarboxylic acid, 1-(3-chlorophthalimido)-,2,2-dimethylhydrazide | — | N | — | 11 |
| Cyclohexanecarboxamide, 1-(3-chlorophthalimido)-N-methyl- | 29 | — | 25 | — |
| Cycloheptanecarboxamide, 1-(3-methylphthalimido)- | 24 | — | 53 | — |
| Cycloheptanecarbox-p-anisidide, 1-(3-methylphthalimido)- | N | — | 33 | — |
| Cycloheptanecarboxylic acid, 1-(3-methylphthalimido)-, 2,2-dimethylhydrazide | N | — | 29 | — |
| Cycloheptanecarboxylic acid, 1-(3-methylphthalimido)-, methyl ester | -20 | — | 17 | — |
| Cyclohexanecarboxylic acid, 1-(3-acetamidophthalimido)- | 14 | — | 22 | — |
| Cyclopentanecarboxamide, 1-(3-chlorophthalimido)-N-methyl- | N | — | 32 | — |
| Cyclopentanecarboxamide, 1-(4-chlorophthalimido)- | 31 | -E.G. | 35 | -E.G. |
| Cyclohexanocarboxamide, 1-(4-methylphthalimido)- | 31 | -E.G. | 50 | -E.G. |
| Cyclohexanecarboxanilide, 4'-chloro-1-(4-ethylphthalimido)- | N | — | 25 | — |
| Cyclohexanecarboxy-o-toluidine, 3'-chloro-1-(4-methylphthalimido)- | 11 | — | 28 | — |
| Cyclohexanecarboxylic acid, 1-(4-methylphthalimido)-,2,2-dimethylhydrazide | 16 | — | 25 | — |
| Cyclopentenecarboxylic acid, 1-(4-methylphthalimido)- | 11 | — | 21 | — |
| Cyclopentanecarboxamide, 1-(3-chlorophthalimido)-N,N-dimethyl- | 19 | — | 19 | — |
| Cyclohexanecarboxy-m-toluidide, 4'-chlor-1-(3-chlorphthalimido)-α,α,α-trifluoro- | 23 | — | 26 | — |
| Cyclohexanecarboxamide, 1-(4-chlorophthalimido)- | 21 | 3 E.G. | 50 | 41 E.G. |
| Cyclohexanecarboxamide, 1-(3-acetamidophathalimide)-N-methyl- | N | -24 | 14 | N |
| Cyclohexanecarbox-p-anisidide, 1-(3-iodophthalimido)- | N | N | 14 | N |
| Cyclohexanecarboxamide, 1-(3-iodophthalimido)- | N | 26 | 28 | 28 |
| Cyclohexanecarboxamide, 1-(3-fluorophthalimido)- | 51 | 39 | 48 | 41 |
| Cyclopentanecarboxamide, 1-(3-methylphthalimido)- | 46 | 48 E.G. | 28 | 27 E.G. |
| Cyclohexanecarboxamide, 1-(3-methylphthalimido)- | 60 | 66 E.G. | 39 | 56 E.G. |
| Cyclooctanecarboxamide, 1-(4-chlorophthalimido- | N | N | N | N |
| Cyclohexanecarboxamide, 1-(3-bromophthalimido)- | 46 | 44 | 47 | 56 |

TABLE XXI-continued

| | 10 lbs/Acre Preemergence | | | |
|---|---|---|---|---|
| | % Increase or Decrease in Height Compared to Control | | | |
| | Soybeans | | Fescue | |
| | First | Final | First | Final |
| Compound | Measurement | Measurement | Measurement | Measurement |
| Cyclohexanecarboxamide, 1-(1,2,3,6-tetrahydro-phthalimido)-1- | N | −23 | 12 | N |
| Cyclohexanecarboxamide, 1-(1-cyclohexene-1,2-dicarboximido)- | 51 | | 61 | |
| Cyclohexanecarboxamide, 3-methyl-1-(3-methyl-phthalimido)-trans(CH$_3$ to CONH$_2$)- | 27 | | 53 | |
| Cyclohexanecarboxylic acid, 3-methyl-1-(3-methylphthalimido)-, trans(CH$_3$ to COOH)- | N | | 11 | |
| Cyclohexanecarboxamide, 1-(hexahydrophthalimido) | N | N | 28 | 26 |
| Cyclohexanecarboxamide, 1-(4-methyl-hexahydro-phthalimido) | N | | 18 | |

Phy = phytotoxic
N = normal
A.G. = acillary growth
D.G. = delayed germination
E.G. = early germination
— = not read for that particular test (either 1st or 2nd)

Special Test - Phthalimide Activity Evaluation

Cotton seed from plants treated at 2 pounds per acre with compounds of the invention at the time of first bloom and seed from untreated controls in the same experiment were planted 5 seeds per 6 inches plastic pot in the spring. There were 4 pots of each type seed, treated and untreated. Treated seedlings broke through the surface on March 17 (19 of 20 seeds emerged, 95% emergence) whereas 7 of 20 seeds of the untreated controls emerged (35% emergence). On March 26 at termination of the test, treated stand was 95% and controls were 50%. These data suggest that treated plants impart better viability to the seed.

EXAMPLE 44

Evaluation of Phthalimides for Plant Growth Regulant Activity

In these tests plastic containers are filled with potting soil to within 3/4 inch of the top. Seeds of Cherry Belle radishes and Kentucky 31 fescue are then placed on the soil surface and covered with ½ inch of potting soil. A tamper is used to level the soil surface and to firm the soil. After planting the pots are sprayed with a 1:1 water acetone mixture containing sufficient compound to provide from about 0.13 to 8.0 pounds per acre of test compound. The treated pots are placed in the greenhouse and watered when needed. Fourteen days after treatment the pots are examined and the plants removed, washed and weighed. Fescue and radishes grown in untreated soil are used as controls and data obtained are reported in Table XXII below.

TABLE XXII

Plant Growth Regulant Activity of Compounds Having the Formula:

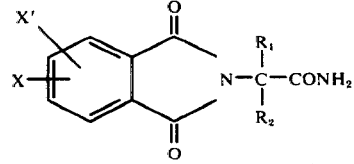

| X | X' | lb/Acre | R$_1$ | R$_2$ | Fescue Fresh Weight (g) | Radish Fresh Weight Whole (g) | Root (g) |
|---|---|---|---|---|---|---|---|
| 3-OC$_2$H$_5$ | 6-OC$_2$H$_5$ | 0.5 | —(CH$_2$)$_5$— | | 17.9 | 60.2 | 46.8 |
| | | 2.0 | | | 21.8 | 59.6 | 45.8 |
| 3-SO$_2$C$_2$H$_5$ | 6-CH$_3$ | 0.5 | —(CH$_2$)$_5$— | | 18.4 | 61.0 | 46.5 |
| | | 2.0 | | | 15.6 | 48.7 | 37.9 |
| 4-CH$_3$ | 5-CH$_3$ | 0.13 | —(CH$_2$)$_5$— | | 17.7 | 61.8 | 48.7 |
| Check | | 0 | | | 17.1 | 55.4 | 41.8 |
| 3-CH$_3$ | 6-CH$_3$ | 2.0 | —(CH$_2$)$_5$— | | 28.4 | 74.5 | 55.9 |
| 3-OC$_2$H$_5$ | 5-OC$_2$H$_5$ | 8.0 | —(CH$_2$)$_5$— | | 25.7 | 76.5 | 59.3 |
| Check | | 0 | | | 26.3 | 62.2 | 44.9 |
| 3-Br | 4-Br | 2.0 | —(CH$_2$)$_5$— | | 34.6 | 55.1 | 39.3 |
| Check | | 0 | | | 27.1 | 61.5 | 44.8 |
| Check | | 0 | | | 27.1 | 61.5 | 44.8 |
| 4-OCH$_3$ | H | 0.13 | —(CH$_2$)$_5$— | | 26.8 | 77.0 | 56.5 |
| 4-OCH$_2$C$_6$H$_5$ | H | 0.5 | —(CH)$_5$— | | 27.9 | 79.3 | 59.5 |

TABLE XXII-continued

Plant Growth Regulant Activity of Compounds Having the Formula:

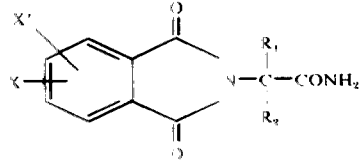

| X | X' | lb/Acre | $R_1$ | $R_2$ | Fescue Fresh Weight (g) | Radish Fresh Weight Whole (g) | Root (g) |
|---|---|---|---|---|---|---|---|
|  |  | 2.0 |  |  | 35.8 | 60.3 | 59.5 |
| 3-CF$_3$ | H | 0.5 | —(CH$_2$)$_5$— |  | 35.4 | 68.5 | 52.1 |
|  |  | 2.0 |  |  | 35.4 | 77.4 | 58.7 |
|  |  | 8.0 |  |  | 41.7 | 54.2 | 39.9 |

We claim:
1. A method for regulating the growth of plants comprising:
applying to the foliage, roots, stems, seeds, seed pieces or to soil in which the plants are grown, an effective plant growth regulating amount of a compound having the formula:

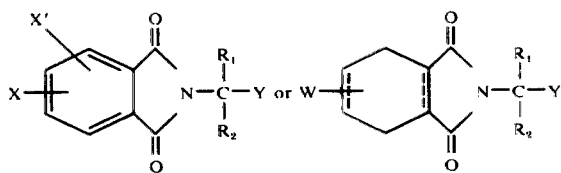

wherein W is hydrogen or lower alkyl $C_1$–$C_4$; X and X' each represent hydrogen, alkyl $C_1$–$C_4$, $CF_3$, alkoxy $C_1$–$C_4$, benzyloxy, di($C_1$–$C_4$) alkylamino, $C_1$–$C_4$ alkylthio, hydroxy, $C_1$–$C_4$ alkylsulfonyl, halogen, alkanoylamino $C_1$–$C_4$ or nitro; Y is —CONHR$_8$, —COOR$_3$, —CONR$_3$R$_4$, —CONHN(R$_5$)$_2$, —CONHN$^+$(R$_6$)$_3$·halide$^-$, or —CN; $R_1$ and $R_2$ each represent alkyl $C_1$–$C_4$ or when taken together with the carbon to which they are attached form cycloalkyl $C_4$–$C_{11}$ optionally substituted with methyl; $R_3$ and $R_4$ each represent hydrogen or alkyl $C_1$–$C_4$; $R_5$ and $R_6$ each represent alkyl $C_1$–$C_2$, $R_8$ is —CH$_3$ or

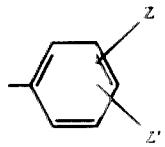

where Z and Z' are hydrogen, alkyl $C_1$–$C_2$, halogen, —CF$_3$ or —OCH$_3$ and $=\!=\!=$ is a single or double bond with the proviso that there be only 0 or 1 double bond in the ring; or mixtures thereof.

2. A method according to claim 1, wherein the active compound is applied to the seeds, seed pieces or soil containing seeds or seed pieces of the plants for which plant growth regulation is desired.

3. A method according to claim 1, wherein the compound is applied to the foliage and stems of the plants for which plant growth regulation is desired.

4. A method according to claim 1, wherein the compound is applied to the roots of the plants for which plant growth regulation is desired.

5. A method according to claim 3, wherein the active compound is applied at the rate of from 0.06 pound to 32 pounds per acre.

6. A method according to claim 2, wherein the active compound is applied at the rate of from 0.06 pound to 32 pounds per acre in the area of application.

7. A method according to claim 1, wherein Y of the formula is —CONR$_3$R$_4$.

8. A method according to claim 1, wherein Y of the formula is —CONHN(R$_5$)$_2$.

9. A method according to claim 1, wherein Y of the formula is —COOR$_3$.

10. A method according to claim 1, wherein the compound applied is 1-(3-chlorophthalimido)cyclohexanecarboxamide; 1-phthalimidocyclohexanecarboxamide; 1-(3-chlorophthalimido)cyclopentanecarboxamide; 1-phthalimidocyclopentanecarboxamide; 1-(4-chlorophthalimido)cyclohexanecarboxamide; 1-(4-methylphthalimido)-1-cyclohexanecarboxamide; 1-(3,4,5,6-tetrahydrophthalimido)-1-cyclohexanecarboxamide, α-isobutyl-α-methyl-α-(3-chlorophthalimido)-acetamide or 1-(3-trifluoromethylphthalimido)cyclohexanecarboxamide.

* * * * *